United States Patent [19]

Parker et al.

[11] Patent Number: 5,608,095
[45] Date of Patent: Mar. 4, 1997

[54] ALKYL-4-SILYL-PHENOLS AND ESTERS THEREOF AS ANTIATHEROSCLEROTIC AGENTS

[75] Inventors: Roger A. Parker; Michael L. Edwards; Mark J. Vaal; James E. Matt, Jr.; Kim S. Chen, all of Cincinnati, Ohio; Mark T. Yates, Ann Arbor, Mich.; Paul S. Wright, Cincinnati; Steven J. Busch, West Chester, both of Ohio

[73] Assignee: Hoechst Marion Roussel, Inc., Cincinnati, Ohio

[21] Appl. No.: 637,968

[22] Filed: Apr. 30, 1996

[51] Int. Cl.$^6$ .................... C07F 7/08; C07F 7/10; C07F 7/18
[52] U.S. Cl. .................... 556/413; 556/418; 556/423; 556/427; 556/437; 556/445; 556/449
[58] Field of Search .................... 556/427, 413, 556/418, 423, 437, 445, 449; 564/63

[56] References Cited

U.S. PATENT DOCUMENTS

| | | |
|---|---|---|
| 3,129,262 | 4/1964 | Laufer . |
| 3,576,883 | 4/1971 | Neuworth . |
| 3,786,100 | 1/1974 | Neuworth . |
| 3,862,332 | 1/1975 | Barnhart et al. . |
| 3,897,500 | 7/1975 | Neuworth . |
| 4,663,314 | 5/1987 | Hayase et al. .................... 514/63 |
| 4,719,237 | 1/1988 | McCaughan . |
| 4,734,527 | 3/1988 | Krauss . |
| 4,772,363 | 9/1988 | Van Effen . |
| 4,861,443 | 8/1989 | Van Effen . |
| 4,900,757 | 2/1990 | Mao et al. . |
| 4,975,467 | 12/1990 | Ku et al. . |
| 5,008,421 | 4/1991 | Brownell et al. .................... 556/449 U X |

(List continued on next page.)

FOREIGN PATENT DOCUMENTS

| | | |
|---|---|---|
| 9460533 | 4/1993 | Australia . |
| 0374048 | 12/1989 | European Pat. Off. . |
| 7330595 | 6/1994 | Japan . |
| 9312089 | 6/1993 | WIPO . |
| 9321914 | 11/1993 | WIPO . |
| 9405333 | 3/1994 | WIPO . |
| 9409772 | 5/1994 | WIPO . |
| 9411027 | 5/1994 | WIPO . |
| 9416094 | 7/1994 | WIPO . |
| 9414786 | 7/1994 | WIPO . |
| 9417828 | 8/1994 | WIPO . |
| 9504749 | 2/1995 | WIPO . |

OTHER PUBLICATIONS

Gotteland et al, *J. Med. Chem.*, 1995, 38, pp. 3207–3216.
Pilewski et al, *Am. J. Respir. Cell Mol. Biol.* vol. 12, pp. 1–3, 1995.

Marui et al, *American Society for Clinical Investigation, Inc.* vol. 92, Oct., 1993, pp. 1866–1874. Vascular Cell Adhesion Molecule–1.

Boschelli et al, *J. Med. Chem.* 1995, 38, pp. 4597–4614. Inhibition of E–Selection–,ICAM–1–, and VCAM–1.

Volin et al, *FASEB Journal*, Federation of American Societies for Experimental Biology, Mar. 10, 1995, vol. 9, No. 4.

Derwent Abstract, 94–322148/40, 1994.

Derwent Abstract, 94–322152/40, 1994.

(List continued on next page.)

*Primary Examiner*—Paul F. Shaver
*Attorney, Agent, or Firm*—William R. Boudreaux

[57] ABSTRACT

This invention relates to compounds of the formula

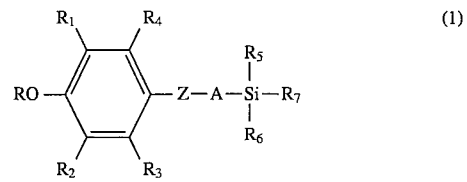

(1)

wherein $R_1$ and $R_6$ are each independently $C_1$–$C_6$ alkyl;

$R_2$, $R_3$ and $R_4$ are each independently hydrogen or $C_1$–$C_6$ alkyl;

R is hydrogen or —C(O)—$(CH_2)_m$—Q wherein Q is hydrogen or —COOH and m is an integer 1, 2, 3 or 4;

Z is a thio, oxy or methylene group;

A is a $C_1$–$C_4$ alkylene group;

$R_5$ and $R_7$ are each independently a $C_1$–$C_6$ alkyl or —$(CH_2)_n$—(Ar) wherein n is an integer 0, 1, 2 or 3; and Ar is phenyl or naphthyl unsubstituted or substituted with one to three substituents selected from the group consisting of hydroxy, methoxy, ethoxy, halogen, trifluoromethyl, $C_1$–$C_6$ alkyl, or —$NR_8R_9$, wherein $R_8$ and $R_9$ are each independently hydrogen or $C_1$–$C_6$ alkyl; with the proviso that when $R_2$ and at least one of $R_5$ or $R_7$ is $C_1$–$C_6$ alkyl, and Ar is not substituted with trifluoromethyl or —$NR_8R_9$, then R is —C(O)—$(CH_2)_m$—Q; or a pharmaceutically acceptable salt thereof; useful for the treatment of atherosclerosis and chronic inflammatory disorders; for inhibiting cytokine-induced expression of VCAM-1 and/or ICAM-1; for inhibiting the peroxidation of LDL lipid; for lowering plasma cholesterol; and as antioxidant chemical additives useful for preventing oxidative deterioration in organic materials.

43 Claims, No Drawings

U.S. PATENT DOCUMENTS

| | | |
|---|---|---|
| 5,061,734 | 10/1991 | Mao et al. |
| 5,112,870 | 5/1992 | Mao et al. |
| 5,155,250 | 10/1992 | Parker et al. ............. 556/427 |
| 5,217,870 | 6/1993 | Hession et al. |
| 5,272,263 | 12/1993 | Hession et al. |
| 5,281,738 | 1/1994 | Parker et al. |
| 5,304,668 | 4/1994 | Parker et al. |
| 5,356,917 | 10/1994 | Panetta . |
| 5,367,056 | 11/1994 | Hession et al. |
| 5,380,747 | 1/1995 | Medford et al. |
| 5,401,883 | 3/1995 | Laskovics et al. |

OTHER PUBLICATIONS

Abstract 009, Pres. made at 211th ACS National Meeting, Mar. 24–28, 1996, Medicinal Chemical Division. Ref. Bioorganic & Medicinal Chemistry Letter, vol. 6, pp. 533–538, 1996.

Derwent Abstract, 94–325887/41, 1994.

Alerting Bulletin 92–324750/49 Abbreviated Abstract for JP06505732-W, 1992.

Alerting Bulletin 92–332847/41 Abbreviated Abstract for JP06505735-W, 1992.

Parthasarathy, et al, "Probucol inhibits oxidative modification of low density lipoprotein", J. Clin. Invest., vol. 77, Feb. 1986, pp. 641–644.

Product Labeling for Lorelco, Physician's Desk Reference, 42nd edition, (1988), Medical Economics Co., Inc. Oradell, N.J.

Steinberg, "Studies on the Mechanism of Action of Probucol", The American Journal of Cardiology, vol. 57, pp. 16H–21H, Jun. 27, 1986.

Satonin et al, "Comparison of gas chromatography and high–performance liquid chromatography for the analysis of probucol in plasma" Journal of Chromatography, 380 (1986) pp. 401–406.

Mao et al, "Monoclonal Antibodies to human . . . I", Clinical Chemistry, vol. 29, No. 11, 1983, pp. 1890–1897.

Mao et al, "Monoclonal Antibodies to human . . . II", Clinical Chemistry, vol. 29, No. 11, 1983, pp. 1898–1903.

Miller, "High Density Lipoproteins and Atherosclerosis", Ann. Rev. Med. 1980 31:97–108.

Brown et al, "Lipoprotein Metabolism in the Macrophage: Implications for Cholesterol Deposition in Atherosclerosis", Ann. Review Biochem., 1983, 52:223–61.

Maciejko et al, "Apolipoprotein A–1 as a marker of angiographically assessed coronary–artery disease", The New England Journal of Medicine, 309:385–389(Aug. 18, 1983).

Mao et al, "Immunochemistry oif human plasma high density lipoproteins . . . " Biochemistry, 1975, 14, p. 4127.

Badimon et al, "Quantification and immunolocalization of apolipoprotein E . . . ", Atherosclerosis, 61 (1986) 57–66.

Mao et al, "Immunochemistry of human plasma high density lipoproteins . . . ", Biochemistry, vol. 14, No. 18, 1975, pp. 4127–4131.

Kita et al, "Probucol prevents the priogression of atherosclerosis in Watanabe heritable . . . " Medical Sciences, vol. 84, pp. 5928–5931, Aug., 1987.

Carew et al, "Antiatherogenic effect of probucol unrelated to its hypocholesterolemic effect: . . . " Medical Sciences, vol. 84, pp. 7725–7729, Nov. 1987.

ALKYL-4-SILYL-PHENOLS AND ESTERS THEREOF AS ANTIATHEROSCLEROTIC AGENTS

BACKGROUND OF THE INVENTION

Coronary heart disease (CHD) remains the leading cause of death in the industrialized countries. Despite recent declines in CHD mortality, CHD is still responsible for more than 500,000 deaths in the U.S. annually. It is estimated that CHD, directly and indirectly, costs the U.S. more than $100 billion a year. The primary cause of CHD is atherosclerosis, a disease characterized by the deposition of lipids in the arterial vessel wall, resulting in a narrowing of the vessel passages and ultimately hardening the vascular system.

Atherosclerosis as manifested in its major clinical complication, ischaemic heart disease, is thought to begin with local injury to the arterial endothelium followed by proliferation of arterial smooth muscle cells from the medial layer to the intimal layer along with deposition of lipid and accumulation of foam cells in the lesion. As the atherosclerotic plaque develops, it progressively occludes more and more blood vessel and can eventually lead to ischaemia or infarction. Therefore, it is desirable to provide a method of inhibiting the progression of atherosclerosis in patients in need thereof.

Hypercholesterolemia is an important risk factor associated with CHD. For example, in December 1984, a National Institute of Health Consensus Development Conference Panel concluded that lowering plasma cholesterol levels (specifically blood levels of low-density lipoprotein cholesterol) will definitely reduce the risk of heart attacks due to CHD. Serum lipoproteins are the carriers for lipids in the circulation. They are classified according to their density: chylomicrons, very low-density lipoproteins (VLDL), low density lipoproteins (LDL) and high-density lipoproteins (HDL). Chylomicrons mainly participate in transporting dietary triglycerides and cholesterol from the intestine to adipose tissue and liver. VLDL deliver endogenously synthesized triglycerides from liver to adipose and other tissues. LDL transports cholesterol to peripheral tissues and regulate endogenous cholesterol levels in those tissues. HDL transports cholesterol from peripheral tissues to the liver. Arterial wall cholesterol is derived almost exclusively from LDL. Brown and Goldstein, *Ann. Rev. Biochem.* 52, 223 (1983); Miller, *Ann. Rev. Med.* 31, 97 (1980)). In patients with low levels of LDL, the development of atherosclerosis is rare. Accordingly, it is desirable to provide a method for reducing plasma cholesterol in patients with hypercholesterolemia or at risk of developing hypercholesterolemia.

Elevated cholesterol levels are also associated with a number of disease states, including restenosis, angina, cerebral arteriosclerosis, and xanthoma. It is desirable to provide a method for reducing plasma cholesterol in patients with, or at risk of developing, restenosis, angina, cerebral arteriosclerosis, xanthoma, and other disease states associated with elevated cholesterol levels.

Vascular cell adhesion molecule-1 (VCAM-1) and intercellular adhesion molecule-1 (ICAM-1) are adhesion molecules in the immunoglobulin superfamily that are upregulated in vascular endothelial and smooth muscle cells by cytokines, such as, for example, interleukin-1 (IL-1), interleukin-4 (IL-4) and tumor necrosis factor-α (TNF-α). Through interaction with the appropriate integrin counter receptor, VCAM-1 and ICAM-1 mediate adhesion and transendothelial migration of leukocytes in inflammatory responses. Inhibitors of VCAM-1 and/or ICAM-1 have therapeutic applications for many types of chronic inflammatory disorders including atherosclerosis, asthma, rheumatoid arthritis, and autoimmune diabetes. For example, in situ hybridization and immunohistochemical analysis of atherosclerotic plaques from patients demonstrate an increased level of adhesion molecules (VCAM-1 and ICAM-1) when compared with non-disease areas. O'Brien, K. D. et al., *J. Clin. Invest.* 92, 945–951 (1993); Davies, M. J. et al., *J. Pathol.* 171, 223–229 (1993); Poston, R. N. et al., *Am. J. Pathol.* 140, 665–673 (1992). An atherogenic diet induces VCAM-1 expression in rabbit aortic endothelium and vascular smooth muscle cells within atheromas. Poston, R. N. et al., Ibid.; Cybulsky, M. I. et al., *Science* 251, 788–791 (1991); Li, H. et al., *Arterioscler. Thromb.* 13, 197–204 (1993). Considering these previous studies, increased VCAM-1 expression is believed to be associated with initiation and progression of atherosclerotic plaques through recruitment of circulating monocytes to the lesion area.

Furthermore, VCAM-1 is also involved as a mediator in other chronic inflammatory disorders such as asthma, rheumatoid arthritis and autoimmune diabetes. For example, it is known that the expression of VCAM-1 and ICAM-1 are increased in asthmatics. Pilewski, J. M. et al., *Am. J. Respir. Cell Mol. Biol* 12, 1–3 (1995); Ohkawara, Y. et al., *Am. J. Respir. Cell Mol. Biol.* 12, 4–12 (1995). Additionally, blocking the integrin receptors for VCAM-1 and ICAM-1 (VLA-4 and LFA-1, respectively) suppressed both early and late phase responses in an ovalbumin-sensitized rat model of allergic airway responses. Rabb, H. A. et al., *Am. J. Respir. Care Med.* 149, 1186–1191 (1994). There is also increased expression of endothelial adhesion molecules, including VCAM-1, in the microvasculature of rheumatoid synovium. Koch, A. E. et al, *Lab. Invest.* 64, 313–322 (1991); Morales-Ducret, J. et al., *Immunol.* 149, 1421–1431 (1992). Neutralizing antibodies directed against VCAM-1 or its counter receptor, VLA-4, can delay the onset of diabetes in a mouse model (NOD mice) which spontaneously develop the disease. Yang, X. D. et al., *Proc. Natl. Acad. Sci. U.S.A.* 90, 10494–10498 (1993); Burkly, L. C. et al., *Diabetes* 43, 523–534 (1994); Baron, J. L. et al., *J. Clin. Invest.* 93, 1700–1708 (1994). Monoclonal antibodies to VCAM-1 can also have a beneficial effect in animal models of allograft rejection, suggesting that inhibitors of VCAM-1 expression may have utility in preventing transplant rejection. Orocz, C. G. et al., *Immuno. Lett.* 32, 7–12 (1992).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea. Koch, A. E. et al., *Nature* 376, 517–519 (1995). Inhibitors of the expression of soluble VCAM-1 have potential therapeutic value in treating diseases with a strong angiogenic component, including tumor growth and metastasis. Folkman, J., and Shing, Y., *J. Biol. Chem.* 10931–10934 (1992).

The promoters for both VCAM-1 and ICAM-1 have been cloned and characterized. For example, both promoters contain multiple DNA sequence elements which can bind the transcription factor, NF-kB. Iademarco, M. F. et al., *J. Biol. Chem.* 267, 16323–16329 (1992); Voraberger, G. et al., *J. Immunol.* 147, 2777–2786 (1991). The NF-kB family of transcription factors is central in the regulation of several genes upregulated within sites of inflammation. The activation of NF-kB as a transcription factor involves dissociation from an inhibitory subunit, IkB, in the cytoplasm. NF-kB subunits translocate to the nucleus, bind to specific DNA sequence elements, and activate transcription of several genes, including VCAM-1 and ICAM-1. Collins T. et al., *Lab. Invest.* 68, 499–508 (1993).

It has been postulated that regulation of VCAM-1 gene expression may be coupled to oxidative stress through specific reduction-oxidation (redox) sensitive transcriptional or posttranscriptional regulatory factors. The antioxidants pyrollidine dithiocarbamate and N-acetylcysteine inhibit cytokine-induced expression of VCAM-1, but not ICAM-1 in vascular endothelial cells. Mauri, N. et al., *J. Clin. Invest.* 92, 1866–1874 (1993). This would indicate that the inhibition of VCAM-1 expression by antioxidants involves some additional factors not involved in the regulation of ICAM-1 expression.

2,6-Di-alkyl-4-silyl-phenols are disclosed as antiatherosclerotic agents by Parker et al. in U.S. Pat. No. 5,155,250, issued Oct. 13, 1992. Furthermore, 2,6-Di-alkyl-4-silyl-phenols are disclosed as serum cholesterol lowering agents in PCT International Publ. No. WO 95/15760, published Jun. 15, 1995.

It would be advantageous to control the release of VCAM-1 and/or ICAM-1, and to treat VCAM-1 and/or ICAM-1 mediated effects. It would also be advantageous to control or treat chronic inflammation, without production of concomitant side effects known to accompany the use of antiinflammatory steroids and non-steroidal antiinflammatory agents.

SUMMARY OF THE INVENTION

The present invention provides compounds of the formula

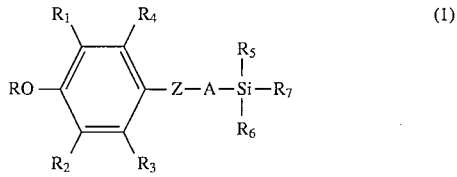

wherein $R_1$ and $R_6$ are each independently $C_1$–$C_6$ alkyl;

$R_2$, $R_3$ and $R_4$ are each independently hydrogen or $C_1$–$C_6$ alkyl;

R is hydrogen or —C(O)—(CH$_2$)$_m$—Q wherein Q is hydrogen or —COOH and m is an integer 1, 2, 3 or 4;

Z is a thio, oxy or methylene group;

A is a $C_1$–$C_4$ alkylene group;

$R_5$ and $R_7$ are each independently a $C_1$–$C_6$ alkyl or —(CH$_2$)$_n$—(Ar) wherein n is an integer 0, 1, 2 or 3; and Ar is phenyl or naphthyl unsubstituted or substituted with one to three substituents selected from the group consisting of hydroxy, methoxy, ethoxy, halogen, trifluoromethyl, $C_1$–$C_6$ alkyl, or —NR$_8$R$_9$, wherein $R_8$ and $R_9$ are each independently hydrogen or $C_1$–$C_6$ alkyl; with the proviso that when $R_2$ and at least one of $R_5$ or $R_7$ is $C_1$–$C_6$ alkyl, and Ar is not substituted with trifluoromethyl or —NR$_8$R$_9$, then R is —C(O)—(CH$_2$)$_m$—Q; or a pharmaceutically acceptable salt thereof.

The present invention also provides a method of inhibiting the peroxidation of LDL lipid in a patient in need thereof comprising administering to said patient an effective antioxidant amount of a compound of formula (1).

The present invention further provides a method for lowering plasma cholesterol level in a patient in need thereof by administration of a plasma cholesterol lowering amount of a compound of formula (1).

The present invention further provides a method for inhibiting the progression of atherosclerosis and/or a method for treating atherosclerosis in a patient in need thereof comprising administering to the patient an antiatherosclerotic amount of a compound of formula (1).

The present invention further provides a method of inhibiting cytokine-induced expression of vascular cell adhesion molecule-1 and/or intercellular adhesion molecule-1 in a patient in need thereof comprising administering to the patient an effective vascular cell adhesion molecule-1 and/or intercellular adhesion molecule-1 inhibiting amount of a compound of formula (1).

The present invention further provides a method of treating a patient afflicted with a chronic inflammatory disease comprising administering to the patient a therapeutically effective amount of a compound of formula (1).

DETAILED DESCRIPTION OF THE INVENTION

As used herein, the term "$C_1$–$C_6$ alkyl" refers to a saturated hydrocarbyl radical of straight, branched or cyclic configuration made up of from one to six carbon atoms. Included within the scope of this term are methyl, ethyl, n-propyl, isopropyl, n-butyl, isobutyl, sec-butyl, tertiarybutyl, n-pentyl, n-hexyl, cyclohexyl and the like.

Likewise, the term "$C_1$–$C_4$ alkylene" refers to a saturated hydrocarbyldiyl radical of straight or branched configuration made up of from one to four carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like.

In those instances wherein $R_5$ is a —(CH$_2$)n—(Ar) radical, the "—(CH$_2$)$_n$—" moiety represents a saturated hydrocarbyldiyl radical of straight chain configuration. The term "n" is defined as an integer 0, 1, 2 or 3. The moiety "—(CH$_2$)$_n$—" thus represents a bond, methylene, 1,2-ethanediyl or 1,3-propanediyl. The "—(Ar)" moiety represents an aryl radical defined as a substituted or unsubstituted phenyl or napthyl group. In those instances wherein the —(Ar) moiety is a substituted aryl, the phenyl or napthyl can bear from 1 to 3 substituents in any position otherwise occupied by a hydrogen atom. Substituents are selected from the group consisting of hydroxy, methoxy, ethoxy, chloro, fluoro and $C_1$–$C_6$ alkyl group. Specifically included within the scope of the term "—(CH$_2$)$_n$—(Ar)" are phenyl; napthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like.

The expression "pharmaceutically acceptable acid addition salts" is intended to apply to any non-toxic organic or inorganic acid addition salt of a suitable compound of formula (1), such as 2,6-di-t-butyl-4[(4-N,N-dimethylaminophenyldimethylsilyl)methyloxy]phenol. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Such salts can exist in either the hydrated or substantially anhydrous form.

The compounds of formula (1) can be prepared by utilizing procedures and techniques well known and appreciated by one of ordinary skill in the art. A general synthetic scheme for preparing compounds of formula (1) wherein Z is sulfur or oxygen is set forth in Scheme A, wherein all substituents, unless otherwise indicated, are previously defined.

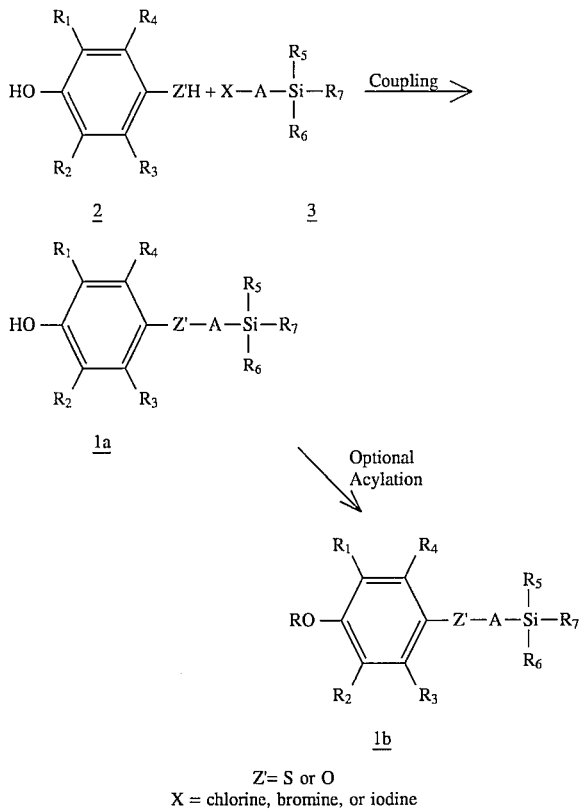

Z' = S or O
X = chlorine, bromine, or iodine

In general, a phenol of structure 1a can be prepared by reacting the appropriate alkyl-4-mercaptophenol or alkylhydroquinone of structure 2 (or suitably protected derivatives) with a non-nucleophilic base, such as sodium hydride, potassium carbonate, cesium carbonate, sodium hydroxide, potassium hydroxide, and the like, and the appropriate haloalkylenesilane of structure 3, such as the appropriate chloroalkylenesilane, in a suitable aprotic solvent, such as acetonitrile, dimethylformamide or dimethylacetamide, or in an aqueous solvent, such as water/2-butanone.

A phenol ester of structure 1b can be prepared by acylating a phenol of structure 1a according to standard acylation techniques. For example, a phenol of structure 1a is dissolved in a suitable aprotic solvent such as acetonitrile, dimethylformamide or dimethylacetamide, or an ethereal solvent such as diethyl ether or dioxane, and treated with a suitable base, such as triethylamine, N-methylmorpholine, sodium hydroxide or sodium hydride. An excess of O-acylating agent is then added at room temperature and the reaction is stirred at room temperature for 1 to 24 hours. Examples of O-acylating agents are acetyl chloride, propionyl chloride, monoethylsuccinylchloride, succinic anhydride, and the like. The product is then purified by techniques well known in the art, such as extractive methods and flash chromatography. Optionally, additional treatment with a suitable base, such as sodium hydroxide with subsequent acidification with a suitable acid, such as hydrochloric acid, followed by extraction and flash chromatography may be performed to provide the phenol ester of structure 1b.

Starting materials for use in the general synthetic procedure outlined in Scheme A are readily available to one of ordinary skill in the art. For example, certain phenol starting materials for various compounds of formula (1) wherein Z is sulfur, such as 2,6-di-tertiarybutyl-4-mercaptophenol and 2-tertiarybutyl-4-mercaptophenol are described in the following patents: U.S. Pat. No. 3,576,883, U.S. Pat. No. 3,952,064, U.S. Pat. No. 3,479,407, U.S. Pat. No. 4,975,467, U.S. Pat. No. 5,155,250 and in Japanese Patent Application 73-28425. Other phenol starting materials for compounds of formula (1) include trimethylhydroquinone and 2,5-di-tertiarybutylhydroquinone which are commercially available.

Silyl starting materials for various compounds of formula (1), such as (trimethylsilyl)methyl iodide, (trimethylsilyl)methyl bromide, (trimethylsilyl)methyl chloride, (1-chloropropyl)trimethylsilane, are described in *Synthesis* 4, 318–19 (1988) and *J. Am. Chem. Soc.* 105, 5665–75 (1983).

Additional methods for preparing suitable silanes include a Grignard reaction. For example, when $R_7$ is a phenyl moiety containing a methoxy substituent, 4-bromoanisole is reacted with magnesium metal to form the Grignard reagent and the reagent is reacted with chlorodimethyl chloromethyl silane to give chloromethyldimethyl-4-methoxy phenyl silane.

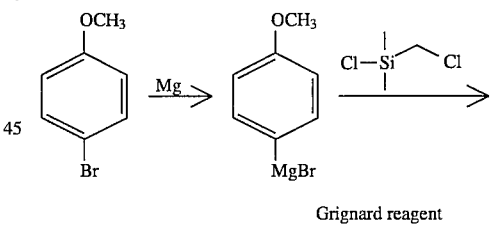

Grignard reagent

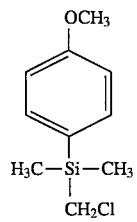

Alternatively, anisole may be lithiated by reaction with n-butyllithium and the lithio compound formed is reacted with chlorodimethyl chloromethyl silane to give chloromethyl dimethyl-2-methoxyphenyl silane.

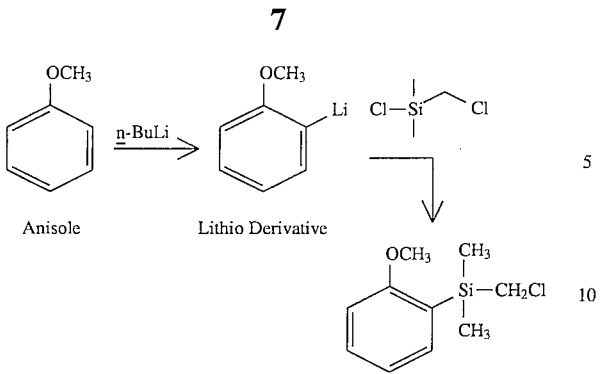

Anisole → Lithio Derivative

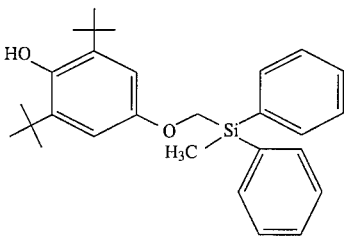

When $R_7$ is a phenyl moiety containing a —$NR_6R_9$ substituent, such as dimethylamine, 4-bromo-N,N-dimethylaniline is reacted with magnesium metal to form the Grignard reagent and the reagent is reacted with chlorodimethyl chloromethyl silane to give 4-N,N-dimethylaminophenyl (dimethyl)chloromethylsilane.

When $R_7$ is a phenyl moiety containing a trifluoromethyl substituent, bromo benzotrifluoride is reacted with magnesium metal to form the Grignard reagent and the reagent is reacted with chlorodimethyl chloromethyl silane to give dimethyl(chloromethyl) trifluoromethylphenylsilane.

When $R_5$ and $R_7$ are both phenyl, about two molar equivalents of phenyl magnesium bromide is reacted with about one molar equivalent of dichloromethyl chloromethyl silane to give methyl diphenylchloromethyl silane.

In those instances where the 1-phenol functionality of a compound of structure 2 may react with the compounds of structure 3 under the conditions of the reaction, the 1-phenol functionality of compound of structure 2 may be blocked with standard phenol blocking agents which are well known and appreciated in the art. The selection and utilization of particular blocking groups are well known to one of ordinary skill in the art. In general, blocking groups should be selected which adequately protect the phenol in question during subsequent synthetic steps and which are readily removable under conditions which will not cause degradation of the desired product.

Examples of suitable phenol protecting groups are ethers, such as methoxymethyl, 2-methoxyethoxymethyl, tetrahydro-pyranyl, t-butyl and benzyl; silyl ethers, such as trimethylsilyl and t-butyldimethylsilyl; esters, such as acetate and benzoate; carbonates, such as methylcarbonate and benzylcarbonate; as well as sulfonates, such as methanesulfonate and toluenesulfonate.

In those instances where $R_1$ and $R_2$ are each t-butyl, the reaction of Scheme A may be conveniently carried out without blocking of the 1-phenol functionality.

The following examples present typical syntheses as described in Scheme A. These examples are understood to be illustrative only and are not intended to limit the scope of the present invention in any way. As used herein, the following terms have the indicated meanings: "g" refers to grams; "mol" refers to moles; "mmol" refers to millimoles; "L" refers to liters; "mL" refers to milliliters; "bp" refers to boiling point; "°C." refers to degrees Celsius; "mm Hg" refers to millimeters of mercury; "mp" refers to melting point; "mg" refers to milligrams; "μM" refers to micromolar; "μg" refers to micrograms; "h" or "hrs." refers to hours, "min" refers to minutes.

EXAMPLE 1

2,6-Di-t-butyl-4-[(diphenylmethylsilyl)methloxy]phenol (MDL 14,599)

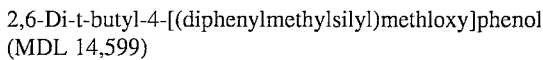

Step a; Preparation of chloro(diphenyl)methylsilane

A solution of bromobenzene (31.5 mL, 0.3 mol) was cooled in dry THF (450 mL) to −60° C. To this solution was added 2.5M n-butyllithium (120 mL, 0.3 mol) dropwise while keeping the reaction temperature below −55° C. Once the addition was complete, chloromethyl(dichloro)methylsilane (18.9 mL, 0.15 mol) was added at such a rate as to keep the reaction temperature below −55° C. The mixture was then warmed to room temperature and ethyl acetate (5 mL) was added to quench any unreacted n-butyllithium. The reaction mixture was poured into water (250 mL) and the organic phase was separated. The organic phase was then washed with water (3×100 mL), subsequently treated with saturated aqueous sodium chloride (3×100 mL), dried with anhydrous magnesium sulfate, filtered and evaporated. Distillation of the resulting pale yellow liquid at 155°–160° C. at 5 mM Hg gave the title compound as a water white liquid (33.1 g, 90% yield). GC/MS confirmed structure and purity (≈99%) of product.

Step b; Preparation of diphenyl(iodomethyl)methylsilane

A solution of chloromethyl(diphenyl)methylsilane (20.0 g, 81 mmol) and sodium iodide (12.3 g, 82 mmol) in 2-butanone (250 mL) was refluxed overnight. Afterwards, the solution was filtered and evaporated. The resulting yellow oil was redissolved in ethyl acetate (250 mL), washed with water (3×100 mL), saturated aqueous sodium chloride (3×100 mL), dried with anhydrous magnesium sulfate, filtered and evaporated. GC/MS of the straw colored oil showed the title compound of sufficient purity (≈99%) to carry on as is.

Step c; Preparation of 2,6-Di-t-butyl-4-[(diphenylmethylsilyl)methyloxy]phenol (MDL 104,5599)

A solution of diphenyl(iodomethyl)methylsilane (9.17 g, 27.1 mmol) and 2,6-di-t-butylbenzhydroquinone (6.0 g, 27 mmol) in dry acetonitrile (250 mL) was thoroughly degassed with nitrogen. To this solution was added potassium carbonate (4.5 g, 32.6 mmol) and the mixture refluxed under nitrogen for 3 days. The reaction mixture was cooled, filtered and evaporated. The resulting oil was redissolved in ethyl acetate (250 mL), washed with water (3×100 mL) and saturated sodium chloride (3×100 mL), dried with anhydrous magnesium sulfate and evaporated. Purification of this oil included distillation to 150° C. @ 5 mM Hg to remove lower boiling impurities followed by several careful chromatographies (silica gel) eluting with hexane and finally recrystallization from methanol to obtain the title compound as a white solid (1.2 g, 10% yield) mp 92°–94° C.

Anal. Calcd. for $C_{28}H_{36}O_2Si$: C, 77.73; H, 8.39; Found: C, 77.66; H, 8.57.

NMR(CDCl$_3$): 7.65–7.60 (m,4H), 7.44–7.33 (m,6H), 6.83 (s,2H), 4.74 (s,1H), 4.02 (s,2H), 1.42 (s,18H), 0.70 (s,3H).

EXAMPLE 2

2,6-Di-t-butyl-4-[(4-N,N-dimethylaminophenyldimethylsilyl)methyloxy]phenol (MDL 104,556)

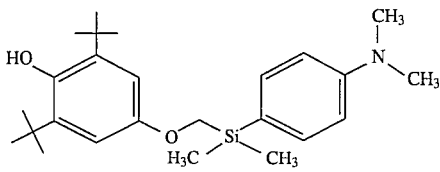

Step a; Preparation of chloromethyl(dimethyl)-4N,N-dimethylaminophenyylsilane

Magnesium turnings (9.7 g, 0.4 g atom) were stirred with a Teflon® paddle overnight under nitrogen. This "activated" magnesium was suspended in dry THF (100 mL) and a crystal of iodine was added. To this suspension was added a solution of 4-bromo-N,N-dimethylaniline (80.0 g, 0.4 mol) in THF (400 mL) at such arate as to maintain a gentle reflux. Once the addition was complete, stirring was continued (~2 hrs.) until nearly all of the magnesium was consumed. A solution of chloro(chloromethyl)dimethylsilane (52.7 mL, 0.4 mol) in dry THF (220 mL) was then added dropwise and the mixture stirred overnight at room temperature. The reaction mixture was then quenched with saturated aqueous ammonium chloride (500 mL) and stirred at room temperature (~2 hrs.). The precipitated magnesium salts were then filtered and the reaction mixture was then diluted with ether (300 mL). The organic phase was separated, washed with water (3×250 mL), saturated aqueous sodium chloride (3×250 mL), dried with anhydrous magnesium sulfate, filtered and evaporated. The resulting brown oil (~90 g) was purified by distillation to give the title compound as a water white liquid (83.5 g, 92% yield, bp 145°C. at 5 mM Hg). GC/MS confirmed structure and purity (~100%) of product.

Step b; Preparation of 4-N,N-dimethylaminophenyl(dimethyl)idomethylsilane

A solution of chloromethyl(dimethyl)-4-N,N-dimethylaminophenylsilane (50.0 g, 0.22 mol) and sodium iodide (33.0 g, 0.22 mol) in 2-butanone (500 mL) was refluxed overnight. The solution was then filtered and evaporated. The resulting liquid was then redissolved in ethyl acetate (500 mL), washed with water (3×200 mL), saturated aqueous sodium chloride (3×200 mL), dried with anhydrous magnesium sulfate, filtered and evaporated. Distillation of the resulting pale yellow liquid at 165° C. at 5 mM Hg gave the title compound as a water white liquid (63.7 g, 91% yield). GC/MS confirmed structure and purity (~100%) of product.

Step c; Preparation of 2,6-Di-t-butyl-4-[(4-N,N-dimethylaminophenyldimethylsilyl)methoxy]phenol (MDL 104,556)

A solution of 4-N,N-dimethylaminophenyl(dimethyl)iodomethylsilane (444 g, 1.39 mol) and 2,6-di-t-butylbenzhydroquinone (309 g, 1.39 mol) in dry acetonitrile (1.5 L) was thoroughly degassed with nitrogen. To this solution was added cesium carbonate (435 g, 1.39 mol) and the mixture refluxed under nitrogen for 24 hours. The reaction mixture was cooled, diluted with ethyl acetate (1.5 L), washed with water (3×500 mL), saturated sodium chloride (3×500 mL), dried with anhydrous magnesium sulfate and evaporated. The resulting brown solid was triturated with methanol (1 L), filtered and dried in vacuo to give a rose colored solid (350 g). This material was recrystallized from ethyl acetate/methanol (~10, 2 L). The material sets up as a waxy white solid which was made homogeneous by mechanically stirring with a Teflon paddle. Filtered this waxy solid, washed with methanol (1 L) that had been cooled in dry ice/acetone and dried in vacuo to give the title compound as a white solid (260 g, 45% yield) mp 115°–117° C.

Anal. Calcd. for $C_{25}H_{39}NO_2Si$: C, 72.59; H, 9.50; N, 3.39; Found: C, 72.47; H, 9.50; N, 3.32.

NMR (CDCl$_3$): 7.47 (d, 2H, J=8.6Hz), 6.81 (s, 2H), 6.75 (d, 2H, J=8.6Hz), 4.70(s,1H),3.69(s,2H), 2.96(s,6H), 1.42(s, 18H), 0.38 (s,6H).

EXAMPLE 3

2,6-Di-t-butyl-4-[(dimethyl-4-trifluoromethylphenylsilyl)methyloxy]phenol (MDL 105,975)

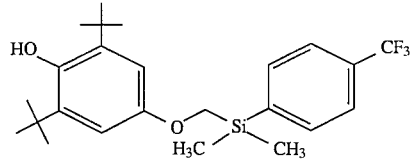

Step a; Preparation of dimethyl-4-trifluoromethylphenylchloromethylsilane

Magnesium metal shavings (9.7 g, 0.4 mol) were placed in a 3-neck flask and stirred overnight under a nitrogen atmosphere with an overhead stirrer to activate the metal. THF (100 mL) and a crystal of iodine were added and a solution of 4-bromobenzotrifluoride (90 g, 0.4 mol) in THF (500 mL) was added at a rate which maintained reflux. The mixture was stirred an additional 4 h, a solution of chlorodimethylchloromethyl-silane (57.2 g, 0.4 mol) in THF (100 mL) was added at a rate which maintained near reflux, and the mixture was stirred overnight at ambient temperature. The mixture was poured into a mixture of ether/aqueous ammonium chloride (1 L each) and the organic layer was isolated, dried and evaporated. Distillation of the residue gave the title compound (53 g, 53%) as a clear liquid, bp 87°–89° C. at 0.1 mm Hg.

Anal. Calcd for $C_{10}H_{12}ClF_3Si$: C, 47.52, H, 4.79; Found: C, 47.31, H, 4.77.

Step b; Preparation of 2,6-Di-t-butyl-4-[(dimethyl-4-trifluoromethylphenylsilyl)methoxy]phenol (MDL 105,975)

A solution of dimethyl(iodomethyl)-4-trifluoromethylphenylsilane (12.0 g, 35 mmol) and 2,6-di-t-butylbenzhydroquinone (6.5 g, 29.2 mmol) in dry acetonitrile (200 mL) was thoroughly degassed with nitrogen. To this solution was added potassium carbonate (4.8 g, 35 mmol) and the mixture refluxed under nitrogen for 36 hours. The reaction mixture was cooled, filtered and evaporated. Redissolved the resulting oil in ethyl acetate (250 mL), washed with water (3×100 mL), saturated sodium chloride (3×100 mL), dried with anhydrous magnesium sulfate and evaporated. Purified this oil by distilling to 200° C. @ 5 mM Hg to remove lower boiling impurities followed by distillation of product (bp 215°–220° C. @ 5 mM Hg). The title compound (6.87 g), which crystallizes on standing, was recrystallized from methanol and dried in vacuo to give a white solid (3.95 g, 31%) mp 107°–110° C.

Anal. Calcd. for $C_{24}H_{33}F_3O_2Si$: C, 65.72; H, 7.58; Found: C, 65.46; H, 7.46.

NMR (CDCl$_3$):7.73 (d,2H,J=7.5 Hz),7.61 (d,2H,J=7.5 Hz), 6.79 (s,2H), 4.74 (s,1H), 3.75 (s,2H), 1.42 (s,18H), 0.44 (s,6H).

EXAMPLE 4

2,6-Di-t-butyl-4-[(dimethyl-3-trifluoromethylphenylsilyl)methyloxy]phenol (MDL 105,726)

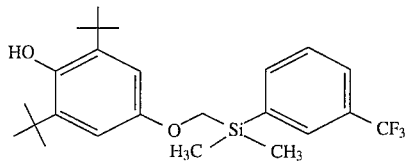

Step a; Preparation of chloromethyl (dimethyl)-3-trifluoromethhylphenylsilane

Magnesium turnings (9.7 g, 0.4 g atom) were stirred with a Teflon® paddle overnight under nitrogen. This "activated" magnesium was suspended in dry THF (100 mL) and a crystal of iodine was added. To this suspension was added a solution of 3-bromo-benzotrifluoride (56 mL, 0.4 mol) in THF (400 mL) at such arate as to maintain a gentle reflux. Once the addition was complete, stirring was continued (~2hrs.) until nearly all of the magnesium was consumed. A solution of chloro(chloromethyl)dimethylsilane (52.7 mL, 0.4 mol) in dry THF (220 mL) was then added dropwise and the mixture stirred overnight at room temperature. The reaction mixture was then quenched with saturated aqueous ammonium chloride (500 mL) and stirred at room temperature (~2 hrs.). The precipitated magnesium salts were then filtered and the reaction mixture was then diluted with ether (300 mL). The organic phase was separated, washed with water (3×250 mL), saturated aqueous sodium chloride (3×250 mL), dried with anhydrous magnesium sulfate, filtered and evaporated. The resulting brown oil (~90 g) was purified by distillation to give the title compound as a water white liquid (69.2 g, 69% yield, bp 95° C. at 5 mm Hg). GC/MS confirmed structure and purity (~100%) of product.

Step b; Preparation of dimethyl (iodomethyl)-3-trifluoromethylphenylsilane

A solution of chloromethyl(dimethyl)-3-trifluoromethylphenylsilane (25.3 g, 0.1 mol) and sodium iodide (15.3 g, 0.102 mol) in 2-butanone (400 mL) was refluxed overnight. The solution was then filtered and evaporated. The resulting liquid was then redissolved in ethyl acetate (500 mL), washed with water (3×250 mL), saturated sodium chloride (3×250 mL), dried with anhydrous magnesium sulfate, filtered and evaporated. The resulting title compound as a pale orange liquid (33.2 g, 97% yield) was sufficiently pure (~96%) to use as is.

Step c; Preparation of 2,6-Di-t-butyl-4-[(dimethyl-3-trifluoromethylphenylsilys)methyloxy]phenol (MDL 105,726)

A solution of dimethyl(iodomethyl)-3-trifluoromethylphenylsilane (15.5 g, 45 mmol)and 2,6-di-t-butylbenzhydroquinone (10 g, 45 mmol) in dry acetonitrile (250 mL) was thoroughly degassed with nitrogen. To this solution was added potassium carbonate (6.2 g, 45 mmol) and the mixture refluxed under nitrogen for 3 days. The reaction mixture was cooled, filtered and evaporated. Redissolved the red oil obtained in ethyl acetate (250 mL), washed with water (3×100 mL), saturated sodium chloride (3×100 mL), dried with anhydrous magnesium sulfate and evaporated. The resulting red oil (~24 g) was distilled to 150° C. @ 5 mm Hg to remove lower boiling impurities. The material left in the pot (~12 g) was flash chromatographed (20% CH$_2$Cl$_2$-hexane), recrystallized twice from methanol and dried in vacuo to give the title compound as a white solid (1.5 g, 8% yield) mp 79°–83° C.

Anal. Calcd. for C$_{24}$H$_{33}$F$_3$O$_2$Si: C, 65.72; H, 7.58; Found: C, 65.62; H, 7.53.

NMR (CDCl$_3$):7.88 (m, 1H), 7.81 (dm,1H,J=7.3 Hz), 7.64 (dm, 1H,J=7.3 Hz), 7.49 (t,1H,J=7.3 Hz), 6.81 (s,2H), 4.75 (s,1H), 3.76 (s,2H), 1.44 (s,18H), 0.46 (s,6H).

EXAMPLE 5

2-t-Butyl-4-[(dimethylphenylsilyl)methyloxy]phenol (MDL 103,491)

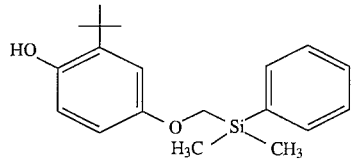

A mixture of 2-t-butyl-1,4-hydroquinone (33.2 g. 0.2 mol), chloromethyldimethylphenylsilane (37.0 g, 0.2 mol), lithium bromide (17.4 g, 0.2 mol), potassium carbonate (27.6 g, 0.2 mol) and acetonitrile (800 mL) was heated to reflux with stirring for 5 days. The mixture was cooled, diluted with water and extracted with ether. The ether layer was washed with water and evaporated to dryness to give a dark oil (66.1 g). The oil was distilled in a kugelrohr. The fraction collected (135°–155° C. @ 0.1 mm Hg) gave 29.9 g of an oil which was redistilled (135°–155° C. @ 0.1 mm Hg) and chromatographed on silica gel (chloroform) afforded 29.2 g of 2-t-butyl-4-[(dimethylphenylsilyl)methyloxy]phenol as a light yellow oil, bp 135° C. (0.1 mm Hg).

Anal: Calcd for C$_{19}$H$_{26}$O$_2$Si: C,72.56; H,8.33; Found: C, 72.32, H, 8.32.

EXAMPLE 6

2,6-Di-t-butyl-4-[(dimethylphenylsilyl)methyloxy]phenol succinic acid ester (MDL 103,076)

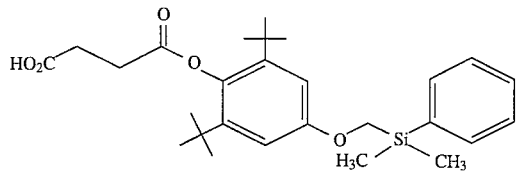

2,6-di-t-butyl-4-[(dimethylphenylsilyl)methyloxy]phenol (5.0 g, 13.5 mmol, U.S. Pat. No. 5,155,250) and sodium hydride (0.6 g of 60% in oil, 15 mmol) in dimethylacetamide (100 mL) was stirred at room temperature for 1 hour. Monoethylsuccinylchloride (2.46 g, 15 mmol) was added to the reaction mixture with stirring. The reaction stirred at room temperature overnight then heated at 90° C. for 2 hours and allowed to cool. The mixture was diluted with water and extracted with ether. The ether layer was washed with water and evaporated to dryness to give 6.6 g of a yellow oil. The oil was combined with 100 mL methanol and heated to reflux. Sodium hydroxide (1.0 g in 20 mL water) was added and the reaction refluxed for 30 minutes then diluted with water and allowed to cool. The aqueous suspension was acidified with conc. hydrochloric acid and the mixture extracted with ether and tetrahydrofuran. The organic layer was separated, evaporated to dryness to give a yellow oil which was crystallized from hexane. 2,6-Di-t-butyl-4-[(dimethylphenylsilyl)methyloxy]phenol succinic acid ester 3.9 g of a white crystalline powder, mp 115°–117° C., was obtained.

Anal: Calcd for C$_{27}$H$_{38}$O$_5$Si: C, 68.90; H, 8.14; Found: C, 68.78, H, 7.93.

EXAMPLE 7

2-t-Butyl-4-[(dimethylphenylsilyl)methyloxy]phenol succinic acid ester (MDL 104,399)

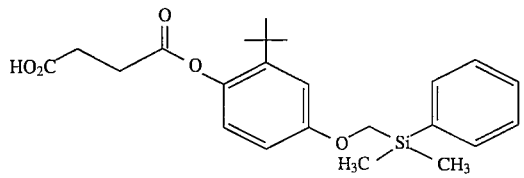

2-t-butyl-4-[(dimethylphenylsilyl)methyloxy]phenol (6.3 g, 20 mmol, Example 5), succinic anhydride (2.2 g., 22 mmol), triethylamine (2.23 g, 22 mmol) and acetonitrile (100 mL) were combined and stirred at room temperature. overnight then heated to reflux for two hours. The cooled mixture was diluted with water and extracted with ether. The ether layer was evaporated to dryness to give a white solid which was recrystallized from acetonitrile. A white solid (6.1 g) mp 92–93 C. of 2-t-butyl-4-[(dimethylphenylsilyl)methyloxy]phenol succinic acid ester was obtained.

Anal: Calcd for $C_{23}H_{30}O_5Si$: C, 66.63, H, 7.29; Found: C, 66.63, H, 7.35.

EXAMPLE 8

2,6-Di-t-butyl-4-[(dimethylphenylsilyl)methylthio]phenol sucinic acid ester (MDL 103,141)

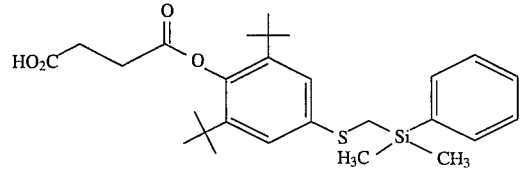

A mixture of 2,6-Di-t-butyl-4-[(dimethylphenylsilyl)methylthio]phenol (10.0 g, 25.9 mmol, U.S. Pat. No. 5,155,250) and sodium hydride (1.03 g of 60% in oil, 25.9 mmol) in tetrahydrofuran (200 mL) was stirred at room temperature for 1 hour. Monoethylsuccinylchloride (4.26, 25.9 mmol) was added to the reaction mixture with stirring. The reaction stirred at room temperature overnight then heated to reflux for 2 hours and allowed to cool. The mixture was diluted with water and extracted with ether. The ether layer was washed with water and evaporated to dryness to give 12.3 g of a waxy solid. The solid was combined with 200 mL methanol and heated to reflux. Sodium hydroxide (5.0 g in 20 mL water) was added and the reaction refluxed for 30 minutes then diluted with water and allowed to cool. The aqueous suspension was acidified with conc. hydrochloric acid and 10.6 g of a solid was collected which was recrystallized from hexan to give 9.3 g of a white crystalline powder, mp 146°–147° C., 2,6-Di-t-Butyl-4-[(Dimethylphenylsilyl)methylthio]phenol Succinic Acid Ester.

Anal. Calcd for $C_{27}H_{38}O_4SSi$; C, 66.62; H, 7.87; Found: C, 66.53; H, 7.68.

EXAMPLE 9

2,6-Di-t-butyl-4-[(trimethylsilyl)methylthio]phenol succinic acid ester (MDL 104,863)

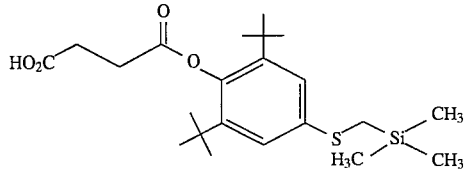

A mixture of 2,6-Di-t-butyl-4-[(trimethylsilyl)methylthio]phenol (4.3 g, 13.2 mmol, U.S. Pat. No. 5,155,250) and sodium hydride (0.48 g of 60% in oil, 12 mmol) in dimethylacetamide (50 mL) was stirred at room temperature. Monoethylsuccinylchloride (2.2 g, 13.2 mmol) was added and the mixture stirred at room temperature for three hours. The mixture was diluted with water and extracted with ether. The ether layer was washed with water and evaporated to dryness to give 5.4 g of a brown oil. The oil was chromatographed on silica gel (chloroform) to give 3.4 g of an oil. The oil was combined with 50 mL methanol and heated to reflux. Sodium hydroxide (0.6 g in 10 mL water) was added and the reaction refluxed for 30 minutes then diluted with water and allowed to cool. The aqueous suspension was acidified with conc. hydrochloric acid and extracted with ether. The ether layer was separated and evaporated to dryness to give 3.0 g of a white solid foam. The solid was chromatographed on silica gel and then recrystallized from ethanol water to give 1.2 g of a white crystalline powder, mp 127°–128° C., 2,6-Di-t-butyl-4-[(trimethylsilyl)methylthio]phenol succinic acid ester.

Anal: Calcd for $C_{22}H_{36}O_4SSi$: C, 62.22; H, 8.55; Found: C, 62.33, H. 8.69.

EXAMPLE 10

2-t-Butyl-4-[(dimethylphenylsilyl)methyloxy]phenol acetic acid ester (MDL 105,443)

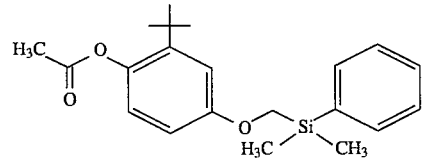

2-t-Butyl-4-[(dimethyl-phenylsilyl)methyloxy]phenol (4.8 g, 15.3 mmol, Example 5), triethylamine (3.04 g, 30 mmol) and 100 mL of ether were combined and stirred at room temperature. Acetyl chloride (2.4 g, 30 mmol) was slowly added with stirring. The mixture was stirred for 4 hours then diluted with water. The layers were separated and the organic layer evaporated to dryness to give 5.6 g of an oil. The oil distilled in a kugelrohr 150°–160° C. (0.1 mm Hg) gave 5.2 g of the title compound as a light yellow oil.

Anal: Calcd for $C_{21}H_{28}O_3Si$: C, 70.74; H, 7.92; Found: C, 71.00; H, 8.09.

EXAMPLE 11

2,6-Di-t-butyl-4-[(dimethylphenylsilyl)methyloxy]phenol acetic acid ester (MDL 103,377)

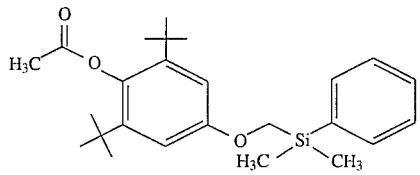

2,6-Di-t-butyl-4-[(dimethylphenylsilyl)methyloxy]phenol (6.2 g, 16.7 mmol, U.S. Pat. No. 5,155,250), sodium hydride (0.67 g of 60% in oil, 16.7 mmol) and 50 ml of dimethylacetamide were combined and stirred at room temperature for 30 minutes. Acetyl chloride (2.6 g, 33.5 mmol) was slowly added to the reaction mixture and the reaction continued overnight. The reaction mixture was diluted with water and ether and the layers separated. The ether layer was evaporated to dryness to give 7.0 g of a waxy solid. Distillation in a kugelrohr (150°–165° C., 0.1 mm Hg) followed by recrystallization from hexane gave 2,6-Di-t-butyl-4-[(dimethyl-phenylsilyl)methyloxy]phenol succinic acid ester acetic acid ester as a white crystalline solid, mp 100°–101° C.

Anal: Calcd for $C_{25}H_{36}O_3Si$: C, 72.76; H, 8.79; Found: C, 72.90; H, 8.59.

EXAMPLE 12

2,3,6-Trimethyl-4-[(dimethylphenylsilyl)methyloxy]phenol acetic acid ester (MDL 103,157)

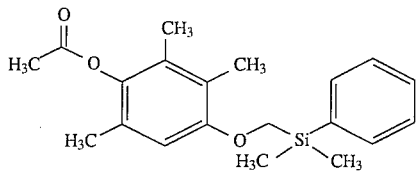

Step a; Preparation of 4-acetoxy-2,3,5-trimethylphenol

Trimethylhydroquinone (15.2 g, 0.1 mol), triethylamine (25.3 g, 0.25 mol) and ether (500 mL) was stirred in an ice bath. Acetylchloride (19.6 g, 0.25 mol) was slowly added with stirring, the reaction was allowed to warm to room temperature for an hour, then diluted with water and the layers separated. Evaporation of the ether layer to dryness gave a tan crystalline solid diacetate (23.1 g, m.p.= 105°–108° C.). The diacetate was dissolved in methanol (300 mL). Strong ammonium hydroxide (11 mL) was added and the mixture was stirred at room temperature overnight. The solvents were distilled off under reduced pressure and the residue dissolved in ether. The ether layer was washed with water and evaporated to dryness to a tan solid (18.4 g). Recrystallization from hexane-ether gave 16.7 g of 4-acetoxy-2,3,5-trimethylphenol, m.p.=106°–107° C.

Step b; Preparation of 2,3,6-Trimethyl-4-[(dimethylphenylsilyl)methyloxy]phenol acetic acid ester (MDL 103,157)

4-Acetoxy-2,3,5-trimethylphenol (8.1 g, 41.7 mmol), chloromethyldimethylphenylsilane (7.7 g, 41.7 mmol), lithium bromide ( 3.6 g, 41.7 mmnol), potassium carbonate (5.8 g, 41.7 mmol) and 150 mL of acetonitrile were combined and heated to reflux with stirring for three days. The mixture was cooled, diluted with water, acidified with conc. hydrochloric acid and extracted into ether. The ether layer was evaporated to dryness to give 14.9 g of a yellow oil. Distillation in a kugelrohr (145°–160° C., 0.1 mm Hg) followed by chromatography on silica gel (chloroform) gave 8.6 g of the title compound as a colorless oil.

Anal: Calcd for $C_{20}H_{26}O_3Si$; C, 71.13; H, 7.65; Found: C, 70.82; H, 7.74.

EXAMPLE 13

2,5-Di-t-butyl-4-[(dimethylphenylsilyl)methyloxy]phenol (MDL 104,962)

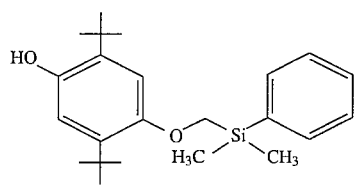

A mixture of 2,5-Di-t-butyl-1,4-hydroquinone (66.7 g, 0.3 mol, Aldrich Chemical Company, Milwaukee, Wis. 53233), chloromethyldimethylphenylsilane (55.4 g, 0.3 mol), lithium bromide (8.7 g, 0.1 mol), potassium carbonate (41.5 g, 0.3 mol), sodium iodide (2.0 g) and acetonitrile (600 mL) was heated to reflux with stirring for 3 days. The mixture was cooled, diluted with water and extracted with ether. The ether layer was washed with water and evaporated to dryness to give 120 g of a dark oil. The oil was distilled in a kugelrohr. The fraction collected (150°–170° C. @ 0.1 mm Hg) gave 20.1 g of an oil which was chromatographed on silica gel (chloroform) afforded 18.3 g of a light yellow oil.

Anal. Calcd for $c_{23}H_{34}O_2Si$; C, 74.54; H, 9.25; Found: C, 74.71; H, 9.27.

EXAMPLE 14

2,5-Di-t-butyl-4-[(dimethylphenylsilyl)methyloxy]phenol acetic acid ester (MDL 106,290)

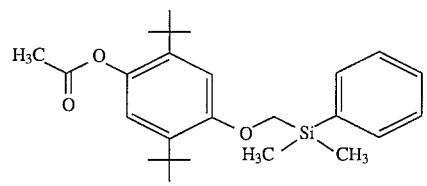

A mixture of 2,5-di-t-butyl-4-[(dimethylphenylsilyl)methyloxy]phenol (7.4 g, 20 mmol, Example 13), triethylamine (2.53 g, 25 mmol) in ether (150 mL) was stirred at room temperature. Acetyl chloride (1.96 g, 25 mmol) was added and the mixture stirred overnight. Water and ether added and the layers separated. Evaporation of the organic layer gave 8.2 g of an amber oil which wads distilled at 150°–180° C. (0.1 mm Hg) in a kugelrohr. Chromatography on silica gel (chloroform) gave 7.5 g of the title compound as a colorless oil.

Anal: Calcd for $C_{25}H_{36}O_3Si$; C, 72.76; H, 8.79; Found: C, 72.99; H, 8.85.

EXAMPLE 15

2-t-Butyl-4-[(dimethylphenylsilyl)methylthio]phenol (MDL 104,571)

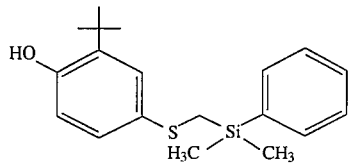

A mixture of 2-t-butyl-4-mercaptophenol (9.1 g, 50 mmol), chloromethyldimethylphenylsilane (9.3 g, 50 mmol), potassium bicarbonate (5.0 g, 50 mmol), potassium carbonate (0.1 g), potassium iodide (2.0 g), and isopropanol (150 mL) was heated to reflux with stirring overnight. The mixture was cooled, diluted with water and ether and the layers separated. The organic layer was evaporated to dryness to give 18.0 g of an amber oil which was distilled at 150°–170° C. (0.1 mm Hg) in a kugelrohr. Chromatography on silica gel (chloroform) gave 11.3 g of a colorless oil.

Anal: Calcd for $C_{19}H_{26}OSSi$; C, 69.03; H, 7.93; Found: C, 69.44; H, 8.05.

EXAMPLE 16

2,3,6-Trimethyl-4-[(dimethylphenylsdilyl)methloxy]phenol (MDL 105,314)

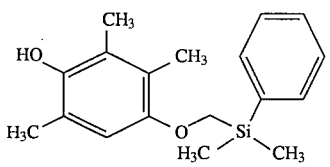

A mixture of trimethylhydroquinone (10.0 g, 66 mmol, Aldrich Chemical Co., Milwaukee, Wis. 53233), chloromethyldimethylphenylsilane (12.2 g, 66 mmol), potassium carbonate (9.12 g, 66 mmol), sodium iodide (9.9 g), and acetonitrile (150 mL) was heated to reflux with stirring for 5 days. The mixture was cooled, diluted with water and ether and the layers separated. The organic layer was evaporated to dryness to give 16.2 g of an amber oil which was distilled at 145°–165° C. (0.1 mm Hg) in a kugelrohr. The oil obtained was chromatographed on silica gel (chlorofoam:carbon tetrachloride 1:1) gave an oil which was distilled at 145°–155° C. (0.1 mm Hg) gave 6.2 g of 2,3,6-trimethyl-4-[(dimethyl-phenylsilyl)methyloxy]phenol as a light straw oil.

Anal: Calcd for $C_{18}H_{24}O_2Si$: C, 71.95; H, 8.05; Found: C, 71.88; H, 8.14.

EXAMPLE 17

2,3,5-Trimethyl-4-[(dimethylphenylsilyl)methyloxy]phenol (MDL 103,653)

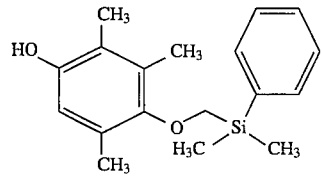

Chromatography of the above reaction product of example (chloroform) followed by distillation at 140°–150° C. (0.1 mm Hg) gave 0.8 g of 2,3,5-trimethyl-4-[(dimethylphenylsilyl)methyloxy]phenol as a colorless oil.

Anal: Calcd for $C_{18}H_{24}O_2Si$: C, 71.95; H, 8.05; Found: C, 71.67; H, 8.08.

EXAMPLE 18

2-t-Butyl-4-[(dimethyl-p-methoxyphenylsilyl)methyloxy]phenol (MDL 106,834)

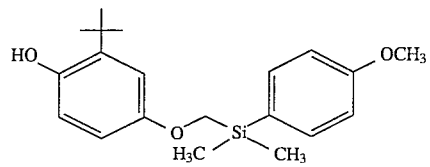

To acetonitrile (250 mL) was added iodomethyldimethyl(4-methoxy)phenyl silane (31.26 g, 102 mmol), cesium carbonate (36.6 g, 112.2 mmol), and t-butylhydroquinone (18.6 g, 112.2 mmol, Aldrich Chemical Co., Milwaukee, Wis. 53233). The mixture was heated to 90° C., and stirred for 42 hours. The mixture was cooled to room temperature, and filtered. The acetonitrile was removed in vacuo, and the residue taken up in ethyl acetate (500 mL). The organic phase was washed with water (200 mL), dried ($MgSO_4$) and concentrated in vacuo. The residue was purified by column chromatography three times on silica gel, eluting with 20:1 hexane/ethyl acetate, affording the title compound as a light brown oil (6.8 g, 19.3% yield).

Elemental: Calc. for $C_{20}H_{28}O_3Si$: C, 69.72; H, 8.19; Found: C, 69.29; H, 8.13.

EXAMPLE 19

2,6-Di-t-butyl-4-[(4-N,N-dimethylaminophenyldimethylsilyl)methyloxy]phenol propionic acid ester

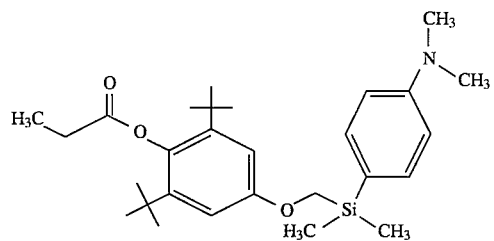

Stir a mixture of 2,6-di-t-butyl-4-[(4-N,N-dimethylaminophenyldimethylsilyl)methyloxy]phenol (8.26 g, 20 mmol, Example 2), triethylamine (2.53 g, 25 mol) in ether (150 mL) at room temperature. Add propionyl chloride (23 g, 25 mmol) and stir the mixture overnight. Add water and ether and separate the layers. Evaporation of the organic layer gives an oil which is then distilled in a kugelrohr. Chromatography on silica gel (chloroform) gives the title compound.

EXAMPLE 20

2,6-Di-t-butyl-4-[(dimethyl-4-trifluoromethylphenylsilyl)methyloxy]phenol butyric acid ester

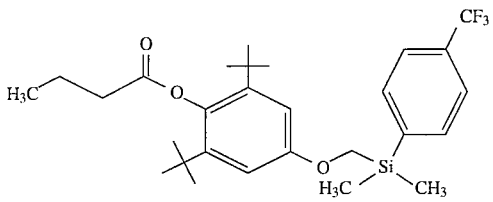

Stir a mixture of 2,6-Di-t-butyl-4-[(dimethyl-4-trifluoromethylphenylsilyl) methyloxy]phenol (8.76 g, 20 mmol, Example 3), triethylamine (2.53 g, 25 mmol) in ether (150 mL) at room temperature. Add butyryl chloride (2.66 g, 25 mmol) and stir the mixture overnight. Add water and ether and separate the layers. Evaporation of the organic layer gives an oil which is then distilled in a kugelrohr. Chromatography on silica gel (chloroform) gives the title compound.

EXAMPLE 21

2,5-Di-t-butyl-4-[(diphenylmethylsilyl)methloxy]phenol

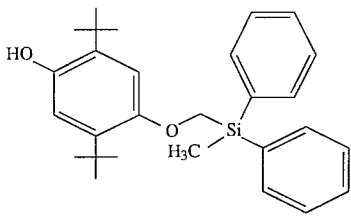

Thoroughly degas a solution of diphenyl (methyl)iodomethylsilane (9.17 g, 27.1 mmol, Example 1, step a) and 2,5-di-t-butylbenzhydroquinone ( 6.0 g, 27 mmol) in dry acetonitrile (250 mL) with nitrogen and add potassium carbonate (4.5 g, 32.6 mmol) in a manner analogous to the procedure described in Example 1, step b, to provide the title compound.

EXAMPLE 22

2-t-butyl-4-[(diphenylmethylsilyl)methyloxy]phenol (MDL 107,917)

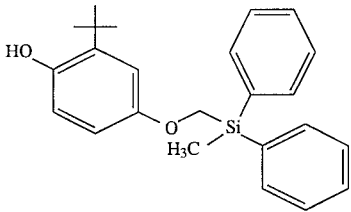

A mixture of 2-t-butylbenzhydroquinone (30 g, 0.18 mol), methyldiphenylchloromethylsilane (45 g, 0.18 mol), cesium carbonate (58 g, 0.18 mol) and lithium bromide (5 g) in acetonitrile (500 mL) was heated at reflux under nitrogen for 7 days, cooled and poured into water (1 L). The organic layer was isolated, dried and evaporated. The residue was placed on a Kugelrohr apparatus and heated at a temperature of 90° C. (0.1 mm) for 2 hrs. The residue was chromatographed (hexane/ethyl acetate 9/1). The purified material was recrystallized with a second run of 0.08 mol to give the product (16.2 g, 12%) as a white solid, mp 100°–101.5° C.

Anal. Calcd for $C_{24}H_{28}O_2Si$: C, 76.55, H, 7.49; Found: C, 76.35, H, 7.49.

EXAMPLE 23

2,6-Di-t-butyl-4-[methyl-di-p-methoxyphenylsilyl)methyloxy]phenol (MDL 108,208)

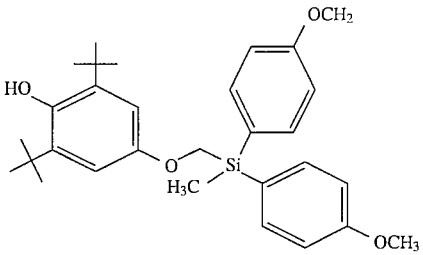

Step a; Preparation of chloromethylbis (4-methoxyphenyl) methylsilane

A solution of 4-bromoanisole (50 mL, 0.4 mol) in THF (500 mL) was added to a suspension of "activated" magnesium (9.7 g, 0.4 g atom) in dry THF (100 mL) containing a crystal of iodine. Then a solution of chloromethyl(dichloro)methylsilane (25.5 mL, 0.2 mol) in dry THF (100 mL) was subsequently added, all in a manner according to example 2, step a, to provide a pale yellow oil. The pale yellow oil was distilled at 200° C. at 5 mm Hg to remove lower boiling impurities. GC/MS confirmed structure and purity (~87%) of the title compound (51.9 g, 85% yield).

Step b; Preparation of iodomethylbis(4-methoxyphenyl)methylsilane

A solution of chloromethylbis(4-methoxyphenyl)methylsilane (51.9 g, 0.169 mol) and sodium iodide (25.5 g, 0.17 mol) in 2-butanone (400 mL) was refluxed overnight. The solution was then filtered and evaporated. The resulting liquid was redissolved in ethyl acetate (500 mL), washed with water (3×250 mL), saturated aqueous sodium chloride (3×250 mL), dried with anhydrous magnesium sulfate, filtered and evaporated. The resulting title compound as a pale orange liquid (63.8 g, 95% yield) was sufficiently pure (~87%) to use as is.

Step c; Preparation of 2,6-Di-t-butyl-4-[(methyl-di-p-methoxyphenyl-silyl)methyloxy]phenol A solution of iodomethylbis(4-methoxyphenyl)methylsilane (53.7 g, 0.135 mol) and 2,6-di-t-butylbenzhydroquinone (30.0 g, 0.135 mol) in dry acetonitrile (500 mL) was thoroughly degassed with nitrogen. To this solution was added potassium carbonate (20.0 g, 0.145 mol) and the mixture was refluxed under nitrogen for 3 days. After this time, GC showed only a trace of product; therefore, lithium bromide (2.0 g) was added and refluxing continued overnight. GC did show ~10% product, so the lithium bromide addition was repeated twice more at daily intervals. Cesium carbonate (2.0 g) was also added at these intervals. After 15 days total reflux, the reaction seemed to be at a stand still of ~30% product. The reaction mixture was cooled, filtered and evaporated. The resulting oil was redissolved in ethyl acetate (500 mL), washed with water (3×250 mL), saturated aqueous sodium chloride (3×250 mL), dried with anhydrous magnesium sulfate and evaporated. The resulting yellow oil crystallized on standing. Trituration of this solid with methanol followed by recrystallization from methanol gave the title compound as a white solid (15.8 g, 24% yield) mp 131°–133° C.

Anal. Calcd. for $C_{30}H_{40}O_4Si$: C, 73.13; H, 8.18; Found: C, 73,14; H, 8.20.

NMR (CDCl$_3$): 7.54 (d, 4H, J=8.5), 6.92 (d, 4H, J=8.5), 6.82 (s, 2H), 4.73 (s, 1H), 3.96 (s, 2H), 3.81 (s, 6H), 1.42 (s, 18H), 0.64 (s, 3H).

EXAMPLE 24

2-t-butyl-4-[(dimethylbenzylsilyl)methyloxy]phenol (MDL 108,804)

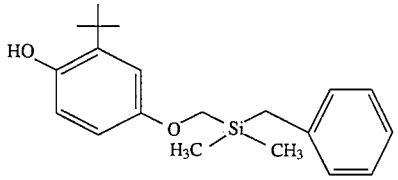

Step a: Preparation of dimethylbenzylchloromethylsilane

A solution of benzylbromide (68.4 g, 0.4 mol) in THF (400 mL) was added to a suspension of "activated" magnesium (9.7 g, 0.4 mol) in dry THF (100 ml) containing a crystal of iodine. Then a solution of dimethylchloromethylsilane (52.7 ml, 0.4 mol) in dry THF (200 ml) was subsequently added, all in a manner according to example 2, step a to provide the title compound. Yield 67%, bp 60°–80° C. at 5 mm Hg.

Anal Calcd for $C_9H_{15}ClOSi$: C, 60.43, H 7.61; Found: C, 60.29, H, 7.77.

Step b; Preparation of 2-t-butyl-4-[(dimethylbenzylsilyl)methyloxy]phenol (MDL 108,804)

A mixture of dimethylbenzylchloromethylsilane (55.2 g, 0.3 mol) and sodium iodide (52 g, 0.35 mol) in acetonitrile (600 mL) was heated at reflux for 24 h, solvent (20 mL) was distilled off to remove any water, and the mixture was cooled to ambient temperature. To the cooled mixture was added 2-t-butylbenzhydroquinone (49.8 g, 0.3 mol) and cesium carbonate (50 g, 0.15 mol). The mixture was heated at 85°–90° C. under an inert atmosphere for 3 days, cooled and poured into a mixture of water/ethyl acetate (1 L each). The organic layer was isolated, dried and evaporated. The residue was heated on a Kugelrohr apparatus at 90° C. for 3 h. The residue was chromatographed (twice with 9/1 hexane/ethyl acetate, then once 1/1). The residue was a liquid (10.5 g, 10%).

Anal. Calcd for $C_{20}H_{28}O_2Si$: C, 73.12, H, 8.59; Found: C, 72.60, H, 8.89.

The following compounds can be prepared by procedures analogous to those described above in Examples 1–24:
2,5-di-t-butyl-4-[(triethylsilyl)methylthio]phenol
2,5-di-t-butyl-4-[(diethylphenylsilyl)methylthio]phenol
2,5-di-t-butyl-4-[(tripropylsilyl)methylthio]phenol
2,5-di-t-butyl-4-[(dipropylphenylsilyl)methylthio]phenol
2,5-di-t-butyl-4-[(triisopropylsilyl)methylthio]phenol
2,5-di-t-butyl-4-[(diisopropylphenylsilyl)methylthio]phenol
2,5-di-t-butyl-4-[(tributylsilyl)methylthio]phenol
2,5-di-t-butyl-4-[(dibutylphenylsilyl)methylthio]phenol
2,5-di-t-butyl-4-[(triisobutylsilyl)methylthio]phenol
2,5-di-t-butyl-4-[(diisobutylphenylsilyl)methylthio]phenol
2,5-di-t-butyl-4-[(tri-t-butylsilyl)methylthio]phenol
2,5-di-t-butyl-4-[(di-t-butylphenylsilyl)methylthio]phenol
2,5-di-methyl-4-[(trimethylsilyl)methylthio]phenol
2,5-di-methyl-4-[(dimethylphenylsilyl)methylthio]phenol
2,5-di-methyl-4-[(dibutylphenylsilyl)methylthio]phenol
2,5-di-methyl-4-[(tri-t-butylsilyl)methylthio]phenol
2,5-di-methyl-4-[(di-t-butylphenylsilyl)methylthio]phenol
2,5-di-ethyl-4-[(trimethylsilyl)methylthio]phenol
2,5-di-ethyl-4-[(dimethylphenylsilyl)methylthio]phenol
2,5-di-ethyl-4-[(tri-t-butylsilyl)methylthio]phenol
2,5-di-ethyl-4-[(di-t-butylphenylsilyl)methylthio]phenol
2,5-di-propyl-4-[(trimethylsilyl)methylthio]phenol
2,5-di-propyl-4-[(dimethylphenylsilyl)methylthio]phenol
2,5-di-isopropyl-4-[(trimethylsilyl)methylthio]phenol
2,5-di-isopropyl-4-[(dimethylphenylsilyl)methylthio]phenol
2,5-di-butyl-4-[(trimethylsilyl)methylthio]phenol
2,5-di-butyl-4-[(dimethylphenylsilyl)methylthio]phenol
2,5-dimethyl-4-[(trimethylsilyl)methyloxy]phenol
2,5-dimethyl-4-[(dimethylphenylsilyl)methyloxy]phenol
2,5-dibutyl-4-[(triethylsilyl)methyloxy]phenol
2,5-dibutyl-4-[(diethylphenylsilyl)methyloxy]phenol
2-t-butyl-4-[(triethylsilyl)methylthio]phenol
2-t-butyl-4-[(diethylphenylsilyl)methylthio]phenol
2-t-butyl-4-[(tripropylsilyl)methylthio]phenol
2-t-butyl-4-[(dipropylphenylsilyl)methylthio]phenol
2-t-butyl-4-[(triisopropylsilyl)methylthio]phenol
2-t-butyl-4-[(diisopropylphenylsilyl)methylthio]phenol
2-t-butyl-4-[(tributylsilyl)methylthio]phenol
2-t-butyl-4-[(dibutylphenylsilyl)methylthio]phenol
2-t-butyl-4-[(triisobutylsilyl)methylthio]phenol
2-t-butyl-4-[(diisobutylphenylsilyl)methylthio]phenol
2-t-butyl-4-[(tri-t-butylsilyl)methylthio]phenol
2-t-butyl-4-[(di-t-butylphenylsilyl)methylthio]phenol
2,3,6-trimethyl-4-[(triethylsilyl)methylthio]phenol
2,3,6-trimethyl-4-[(diethylphenylsilyl)methylthio]phenol
2,3,6-trimethyl-4-[(tripropylsilyl)methylthio]phenol
2,3,6-trimethyl-4-[(dipropylphenylsilyl)methylthio]phenol
2,3,6-trimethyl-4-[(triisopropylsilyl)methylthio]phenol
2,3,6-trimethyl-4-[(diisopropylphenylsilyl)methylthio]phenol
2,3,6-trimethyl-4-[(tributylsilyl)methylthio]phenol
2,3,6-trimethyl-4-[(dibutylphenylsilyl)methylthio]phenol
2,3,6-trimethyl-4-[(triisobutylsilyl)methylthio]phenol
2,3,6-trimethyl-4-[(diisobutylphenylsilyl)methylthio]phenol
2,3,6-trimethyl-4-[(tri-t-butylsilyl)methylthio]phenol
2,3,6-trimethyl-4-[(di-t-butylphenylsilyl)methylthio]phenol
2,3,6-trimethyl-4[(4-aminophenyldimethylsilyl)methyloxy]phenol
2,3,5-trimethyl-4-[(triethylsilyl)methylthio]phenol
2,3,5-trimethyl-4-[(diethylphenylsilyl)methylthio]phenol
2,3,5-trimethyl-4-[(tripropylsilyl)methylthio]phenol
2,3,5-trimethyl-4-[(dipropylphenylsilyl)methylthio]phenol
2,3,5-trimethyl-4-[(triisopropylsilyl)methylthio]phenol
2,6-di-t-butyl-4-[(4-N-methylaminophenyldimethylsilyl)methyloxy]phenol
2,6-di-t-butyl-4-[(4-N-methyl-N-ethylaminophenyldimethylsilyl)methyloxy]phenol
2,6-di-t-butyl-4-[(4-aminophenyldimethylsilyl)methylthio]phenol
2,6-di-t-butyl-4-[(4-N-methylaminophenyldimethylsilyl)methylthio]phenol
2,6-di-t-butyl-4-[(4-N-methyl-N-ethylaminophenyldimethylsilyl)methylthio]phenol
2,5-di-t-butyl-4-[(4-N,N-dimethylaminophenyldimethylsilyl)methyloxy]phenol
2,5-di-t-butyl-4-[(4-aminophenyldimethylsilyl)methyloxy]phenol
2,5-di-t-butyl-4-[(4-N-methylaminophenyldimethylsilyl)methyloxy]phenol
2,5-di-t-butyl-4-[(4-N-methyl-N-ethylaminophenyldimethylsilyl)methyloxy]phenol
2,5-di-t-butyl-4-[(4-aminophenyldimethylsilyl)methylthio]phenol 2,5-di-t-butyl-4-[(4-N-methylaminophenyldimethylsilyl)methylthio]phenol
2,5-di-t-butyl-4-[(4-N-methyl-N-ethylaminophenyldimethylsilyl)methylthio]phenol
2-t-butyl-4-[(4-N,N-dimethylaminophenyldimethylsilyl)methyloxy]phenol
2-t-butyl-4-[(4-aminophenyldimethylsilyl)methyloxy]phenol
2-t-butyl-4-[(4-N-methylaminophenyldimethylsilyl)methyloxy]phenol
2-t-butyl-4-[(4-N-methyl-N-ethylaminophenyldimethylsilyl)methyloxy]phenol
2-t-butyl-4-[(4-aminophenyldimethylsilyl)methylthio]phenol
2-t-butyl-4-[(4-N-methylaminophenyldimethylsilyl)methylthio]phenol
2-t-butyl-4-[(4-N-methyl-N-ethylaminophenyldimethylsilyl)methylthio]phenol
2,3,6-trimethyl-4-[(4-N,N-dimethylaminophenyldimethylsilyl)methyloxy]phenol
2,3,6-trimethyl-4-[(4-aminophenyldimethylsilyl)methyloxy]phenol
2,3,6-trimethyl-4-[(4-N-methylaminophenyldimethylsilyl)methyloxy]phenol
2,3,6-trimethyl-4-[(4-N-methyl-N-ethylaminophenyldimethylsilyl)methyloxy]phenol
2,3,6-trimethyl-4-[(4-aminophenyldimethylsilyl)methylthio]phenol
2,3,6-trimethyl-4-[(4-N-methylaminophenyldimethylsilyl)methylthio]phenol
2,3,6-trimethyl-4-[(4-N-methyl-N-ethylaminophenyldimethylsilyl)methylthio]phenol
2,3,5-trimethyl-4-[(4-N,N-dimethylaminophenyldimethylsilyl)methyloxy]phenol
2,3,5-trimethyl-4-[(4-aminophenyldimethylsilyl)methyloxy]phenol
2,3,5-trimethyl-4-[(4-N-methylaminophenyldimethylsilyl)methyloxy]phenol
2,3,5-trimethyl-4-[(4-N-methyl-N-ethylaminophenyldimethylsilyl)methyloxy]phenol
2,3,5-trimethyl-4-[(4-aminophenyldimethylsilyl)methylthio]phenol
2,3,5-trimethyl-4-[(4-N-methylaminophenyldimethylsilyl)methylthio]phenol
2,3,5-trimethyl-4-[(4-N-methyl-N-ethylaminophenyldimethylsilyl)methylthio]phenol
2,3,5-trimethyl-4-[(diphenylmethylsilyl)methyloxy]phenol
2,6-di-t-butyl-4-[(dimethyl-4-trifluoromethylphenylsilyl)methyloxy]phenol
2,3,6-trimethyl-4-[(dimethyl-4-trifluoromethylphenylsilyl)methyloxy]phenol
2,6-di-t-butyl-4-[(dimethyl-3-trifluoromethylphenylsilyl)methyloxy]phenol
2,6-di-t-butyl-4-[(dimethylphenylsilyl)methyloxy]phenol propionic acid ester
2,6-di-t-butyl-4-[(dimethylphenylsilyl)methyloxy]phenol butyric acid ester
2,6-di-t-butyl-4-[(4-N,N-dimethylaminophenyldimethylsilyl)methyloxy]phenol acetic acid ester
2,6-di-t-butyl-4-[(4-N,N-dimethylaminophenyldimethylsilyl)methyloxy]phenol succinic acid ester
2,6-di-t-butyl-4-[(4-N,N-dimethylaminophenyldimethylsilyl)methyloxy]phenol butyric acid ester
2,6-di-t-butyl-4-[(4-N-methylaminophenyldimethylsilyl)methyloxy]phenol acetic acid ester
2,6-di-t-butyl-4-[(4-N-methyl-N-ethylaminophenyldimethylsilyl)methyloxy]phenol succinic acid ester
2,6-di-t-butyl-4-[(4-aminophenyldimethylsilyl)methylthio]phenol acetic acid ester
2,6-di-t-butyl-4-[(4-N-methylaminophenyldimethylsilyl)methylthio]phenol succinic acid ester
2,6-di-t-butyl-4-[(4-N-methyl-N-ethylaminophenyldimethylsilyl)methylthio]phenol propionic acid ester
2,5-di-t-butyl-4-[(4-N,N-dimethylaminophenyldimethylsilyl)methyloxy]phenol acetic acid ester
2,5-di-t-butyl-4-[(4-N,N-dimethylaminophenyldimethylsilyl)methyloxy]phenol succinic acid ester
2,5-di-t-butyl-4-[(4-N,N-dimethylaminophenyldimethylsilyl)methyloxy]phenol propionic acid ester
2,3,6-trimethyl-4-[(4-N,N-dimethylaminophenyldimethylsilyl)methyloxy]phenol butyric acid ester
2,3,6-trimethyl-4-[(4-N-methylaminophenyldimethylsilyl)methyloxy]phenol acetic acid ester
2,3,6-trimethyl-4-[(4-N-methyl-N-ethylaminophenyldimethylsilyl)methyloxy]phenol succinic acid ester
2,3,5-trimethyl-4-[(4-aminophenyldimethylsilyl)methylthio]phenol acetic acid ester
2,3,5-trimethyl-4-[(4-N-methylaminophenyldimethylsilyl)methylthio]phenol succinic acid ester
2,3,5-trimethyl-4-[(4-N-methyl-N-ethylaminophenyldimethylsilyl)methylthio]phenol propionic acid ester
2,5-di-t-butyl-4-[(triethylsilyl)methylthio]phenol acetic acid ester
2,5-di-t-butyl-4-[(diethylphenylsilyl)methylthio]phenol succinic acid ester
2,5-di-t-butyl-4-[(tripropylsilyl)methylthio]phenol acetic acid ester
2,5-di-t-butyl-4-[(dipropylphenylsilyl)methylthio]phenol acetic acid ester
2,5-di-t-butyl-4-[(triisopropylsilyl)methylthio]phenol propionic acid ester
2,5-di-t-butyl-4-[(diisopropylphenylsilyl)methylthio]phenol butyric acid ester
2,5-di-t-butyl-4-[(tributylsilyl)methylthio]phenol succinic acid ester
2,5-di-t-butyl-4-[(dibutylphenylsilyl)methylthio]phenol acetic acid ester
2,5-di-t-butyl-4-[(triisobutylsilyl)methylthio]phenol acetic acid ester
2,5-di-t-butyl-4-[(diisobutylphenylsilyl)methylthio]phenol succinic acid ester
2,5-di-t-butyl-4-[(tri-t-butylsilyl)methylthio]phenol succinic acid ester
2,5-di-t-butyl-4-[(di-t-butylphenylsilyl)methylthio]phenol acetic acid ester
2,3,6-trimethyl-4-[(diphenylmethylsilyl)methyloxy]phenol acetic acid ester
2,3,5-trimethyl-4-[(diphenylmethylsilyl)methyloxy]phenol acetic acid ester
2,6-di-t-butyl-4-[(dimethyl-4-trifluoromethylphenylsilyl)methyloxy]phenol acetic acid ester
2,3,6-trimethyl-4-[(dimethyl-4-trifluoromethylphenylsilyl)methyloxy]phenol acetic acid ester
2,6-di-t-butyl-4-[(dimethyl-3-trifluoromethylphenylsilyl)methyloxy]phenol succinic acid ester A general synthetic scheme for preparing compounds of formula 1 wherein Z is methylene is set forth in Scheme B, wherein all substituents, unless otherwise indicated, are previously defined.

SCHEME B

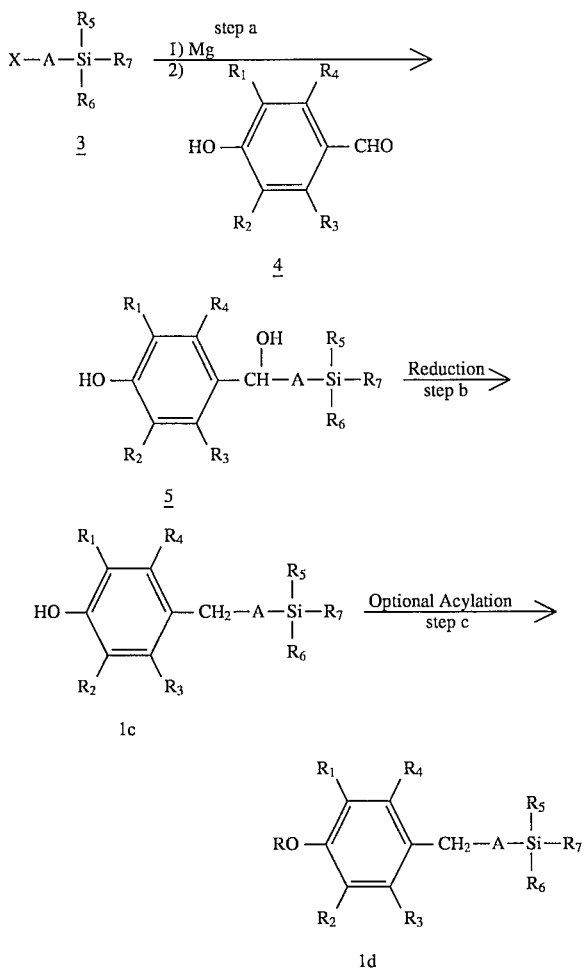

In general, a phenol of structure 1c can be prepared according to Scheme B in a two-step process. In step a, the appropriate haloalkylenesilane of structure 3 is reacted with magnesium metal in a suitable aprotic solvent, such as ethyl ether, in order to form the magnesium halide salt. The magnesium halide salt (Grignard reagent) is then reacted with the appropriate alkyl-4-hydroxy-benzaldehyde of structure 4 (or a suitably protected derivative) to give the alcohol of structure 5. In step b, the alcohol of structure 5 can be reduced to the desired phenol of structure 1b by a variety of reduction techniques and procedures as are well known and appreciated in the art. For example, the alcohol of structure 5 can be reduced by means of a Birch reduction by reacting it with sodium in liquid ammonia.

A phenol ester of structure 1d can be prepared by acylating a phenol of structure 1c according to standard acylation techniques as described previously in Scheme A.

Starting materials for use in the general synthetic procedures outlined in Scheme B are readily available or can readily be prepared according to standard techniques and procedures. Where necessary to prevent undesired side reactions, the 1-phenol functionality of the alkyl-4-hydroxy-benzaldehyde of structure 4 in Scheme B may be blocked prior to the Grignard reaction with a standard phenol blocking agent as described previously in Scheme A.

The following example presents a typical synthesis as described in Scheme B. This example is understood to be illustrative only and is not intended to limit the scope of the present invention in any way.

EXAMPLE 25

2,3,6-Dimethyl-4-[2-(trimethylsilyl)ethyl]phenol

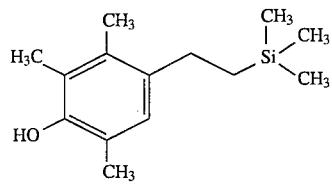

Step a

Mix magnesium turnings (240 mg, 10 mmol) and anhydrous ethyl ether under an inert atmosphere. Add a solution of chloromethyltrimethylsilane (1.9 g, 10 mmol) in anhydrous ethyl ether. Stir until the magnesium metal dissolves. Add a solution of 2,3,5-trimethyl-4-hydroxybenzaldehyde (1.7 g, 10 mmol) in anhydrous ethyl ether. Stir until reaction is complete. Cool the reaction mixture to 0° C. and add saturated ammonium chloride solution. Separate the ether layer, wash with water and dry (MgSO$_4$). Evaporate to give 4-hydroxy-2,3,5-trimethyl-α-[(trimethylsilyl)methyl]benzenemethanol and purify by silica gel chromatrography.

Step b

Mix sodium metal (520 mg, 22.6 mmol) and liquid ammonia (13 mL). To this solution add, by dropwise addition, a solution of 4-hydroxy-2,3,5-trimethyl-α-[(trimethylsilyl)methyl]benzenemethanol (2.37 g, 10 mmol) in ethyl alcohol (0.5 g) and ethyl ether (5 ml). After the blue color disappears, cautiously add water (13 mL), extract with ethyl ether, dry (MgSO$_4$), and evaporate the solvent. Purify the residue by silica gel chromatography to yield the title compound.

Alternatively, compounds of formula (1) wherein Z is methylene can be prepared according to the procedure set forth in Scheme C, wherein all substituents, unless otherwise indicated, are previously described.

SCHEME C

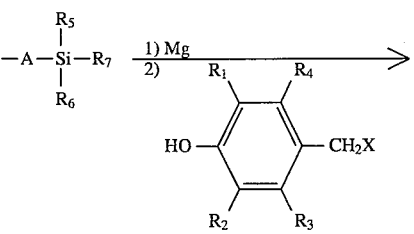

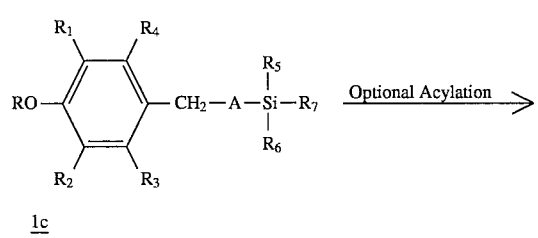

-continued
SCHEME C

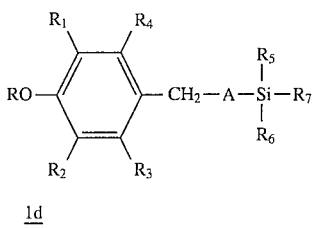

1d

In general, a phenol of structure 1b can be prepared by first reacting the appropriate haloalkylenesilane of structure 3 with magnesium metal in an suitable aprotic solvent, such as ethyl ether, in order to form the magnesium halide salt. The magnesium halide salt (Grignard Reagent) is then reacted with the appropriate alkyl-4-hydroxy-benzylhalide of structure 6 (or a suitably protected derivative) to give the desired phenol of structure 1c.

A phenol ester of structure 1d can be prepared by acylating a phenol of structure 1c according to standard acylation techniques as described previously in Scheme A.

Starting materials for use in the general synthetic procedures outlined in Scheme C are readily available or can readily be prepared according to standard techniques and procedures. For example, the preparation of 3,5-dimethyl-4-acetoxy-benzylbromide is described in *Tetrahedron* 33, 3097–103 (1977). 3,5-Dimethyl-4-acetoxybenzylbromide can be converted to the corresponding phenolic starting material by standard hydrolyric procedures.

Where necessary to prevent undesired side reactions, the 1-phenol functionality of the alkyl-4-hydroxybenzylhalide of structure 6 in Scheme C may be blocked prior to the Grignard reaction with a standard phenol blocking agent as described previously in Scheme A.

The following examples present typical syntheses as described in Scheme C. These examples are understood to be illustrative only and are not intended to limit the scope of the present invention in any way.

EXAMPLE 26

2,6-Diethyl-4-[(4-N,N-dimethylaminophenyldimethylsilyl)ethyl]phenol

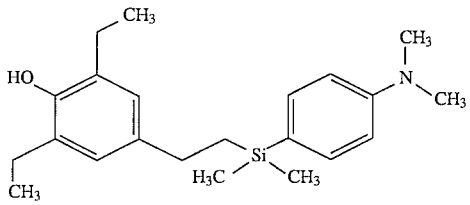

Mix magnesium turnings (240 mg, 10 mmol) and anhydrous ethyl ether under an inert atmosphere. Add a solution of 4-N,N-dimethylaminophenyl(dimethyl) iodomethylsilane (3.19 g, 10 mmol, Example 2) in anhydrous ethyl ether. Stir until the magnesium metal dissolves. Add a solution of 4-bromomethyl-2,6-diethylphenol (2.43 g, 10 mmol) in anhydrous ethyl ether and reflux the mixture until the reaction is complete. Pour onto a mixture of ice/hydrochloric acid and separate the layers. Wash the ethereal layer with water, dry (MgSO$_4$) and evaporate to give the title compound which is purified by silica gel chromatography.

EXAMPLE 27

2,6-Diethyl-4-[(4-N,N-dimethylaminophenyldimethylsilyl)ethyl]phenol acetic acid ester

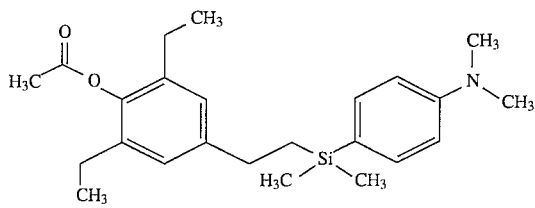

Stir a mixture of 2,6-diethyl-4-[(4-N,N-dimethylaminophenyldimethylsilyl)ethyl]phenol (7.1 g, 20 mmol, Example 26), triethylamine (2.53 g, 25 mmol) in ether (150 ml) at room temperature. Add acetyl chloride (1.96 g, 25 mmol) and stir the mixture overnight. Add water and ether and separate the layers. Evaporation of the organic layer gives an oil which is distilled in a kugelrohr. Chromatography on silica gel (chloroform) gives the title compound.

EXAMPLE 28

2,6-Di-t-butyl-4-[(diphenylmethylsilyl)ethyl]phenol

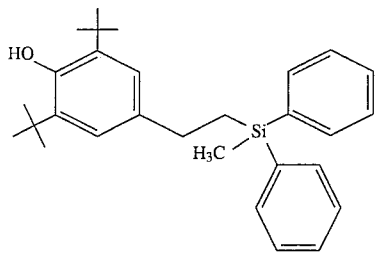

A solution of diphenyl(methyl)chloromethylsilane (1.85 g, 10 mmol, Example 1) in anhydrous ethyl ether is reacted with a mixture of magnesium turnings (240 mg, 10 mmol) and anhydrous ethyl ether and subsequently reacted with a solution of 4-bromomethyl-2,6-di-t-butylphenol (2.9 g, 10 mmol, Maybridge # MB 00185) in anhydrous ethyl ether in a manner analogous to the procedure described in Example 26 to provide the title compound.

The following compounds can be prepared by procedures analogous to those described above in Examples 25–28:
2,5-dipropyl-4-[2-(trimethylsilyl)ethyl]phenol
2,5-dipropyl-4-[2-(dimethylphenylsilyl)ethyl]phenol
2,5-diisopropyl-4-[2-(trimethylsilyl)ethyl]phenol
2,5-diisopropyl-4-[2-(dimethylphenylsilyl)ethyl]phenol
2,5-diisobutyl-4-[2-(trimethylsilyl)ethyl]phenol
2,5-diisobutyl-4-[2-(dimethylphenylsilyl)ethyl]phenol
2,5-dibutyl-4-[2-(trimethylsilyl)ethyl]phenol
2,5-dibutyl-4-[2-(dimethylphenylsilyl)ethyl]phenol
2,5-di-t-butyl-4-[2-(trimethylsilyl)ethyl]phenol
2,5-di-t-butyl-4-[2-(dimethylphenylsilyl)ethyl]phenol
2,5-di-t-butyl-4-[2-(tri-t-butylsilyl)ethyl]phenol
2,5-di-t-butyl-4-[2-(di-t-butylphenylsilyl)ethyl]phenol
2,5-dimethyl-4-[2-(trimethylsilyl)ethyl]phenol
2,5-dimethyl-4-[2-(dimethylphenylsilyl)ethyl]phenol
2-t-butyl-4-[2-(trimethylsilyl)ethyl]phenol
2-t-butyl-4-[2-(dimethylphenylsilyl)ethyl]phenol
2-t-butyl-4-[2-(trimethylsilyl)ethyl]phenol
2-t-butyl-4-[2-(dimethylphenylsilyl)ethyl]phenol
2-t-butyl-4-[2-(trimethylsilyl)ethyl]phenol
2-t-butyl-4-[2-(dimethylphenylsilyl)ethyl]phenol
2-t-butyl-4-[2-(trimethylsilyl)ethyl]phenol 2-t-butyl-4-[2-(dimethylphenylsilyl)ethyl]phenol
2,3,5-tri-t-butyl-4-[2-(trimethylsilyl)ethyl]phenol
2,3,5-tri-t-butyl-4-[2-(dimethylphenylsilyl)ethyl]phenol
2,3,5-tri-t-butyl-4-[2-(tri-t-butylsilyl)ethyl]phenol
2,3,5-tri-t-butyl-4-[2-(di-t-butylphenylsilyl)ethyl]phenol
2,3,6-trimethyl-4-[2-(trimethylsilyl)ethyl]phenol
2,3,6-trimethyl-4-[2-(dimethylphenylsilyl)ethyl]phenol
2,6-di-t-butyl-4-[(4-N-methylaminophenyldimethylsilyl)ethyl]phenol
2,6-di-t-butyl-4-[(4-N-methyl-N-ethylaminophenyldimethylsilyl)ethyl]phenol
2,6-di-t-butyl-4-[(4-aminophenyldimethylsilyl)ethyl]phenol
2,5-di-t-butyl-4-[(4-N,N-dimethylaminophenyldimethylsilyl)ethyl]phenol
2,5-di-t-butyl-4-[(4-aminophenyldimethylsilyl)ethyl]phenol
2,5-di-t-butyl-4-[(4-N-methylaminophenyldimethylsilyl)ethyl]phenol
2,5-di-t-butyl-4-[(4-N-methyl-N-ethylaminophenyldimethylsilyl)ethyl]phenol
2,6-di-t-butyl-4-[(dimethylphenylsilyl)ethyl]phenol propionic acid ester
2,6-di-t-butyl-4-[(dimethylphenylsilyl)ethyl]phenol butyric acid ester
2,6-di-t-butyl-4-[(4-N,N-dimethylaminophenyldimethylsilyl)ethyl]phenol acetic acid ester
2,6-di-t-butyl-4-[(4-N,N-dimethylaminophenyldimethylsilyl)ethyl]phenol succinic acid ester
2,6-di-t-butyl-4-[(4-N,N-dimethylaminophenyldimethylsilyl)ethyl]phenol butyric acid ester
2,6-di-t-butyl-4-[(4-N-methylaminophenyldimethylsilyl)ethyl]phenol acetic acid ester
2,6-di-t-butyl-4-[(4-N-methyl-N-ethylaminophenyldimethylsilyl)ethyl]phenol succinic acid ester
2,6-di-t-butyl-4-[(4-aminophenyldimethylsilyl)ethyl]phenol acetic acid ester
2,5-di-t-butyl-4-[(triethylsilyl)ethyl]phenol acetic acid ester
2,5-di-t-butyl-4-[(diethylphenylsilyl)ethyl]phenol succinic acid ester
2,3,6-trimethyl-4-[(diphenylmethylsilyl)methyloxy]phenol acetic acid ester
2,3,5-trimethyl-4-[(diphenylmethylsilyl)methyloxy]phenol acetic acid ester
2,6-di-t-butyl-4-[(dimethyl-4-trifluoromethylphenylsilyl)methyloxy phenol acetic acid ester
2,3,6-trimethyl-4-[(dimethyl-4-trifluoromethylphenylsilyl)methyloxy phenol acetic acid ester
2,6-di-t-butyl-4-[(dimethyl-3-trifluoromethylphenylsilyl)methyloxy phenol succinic acid ester.

It is understood that compounds of formula (1) may exist in various stereoisomeric forms. All stereoisomeric forms which are consistent with the above structural formulas, as interpreted according to standard conventions for expressing stereoisomeric structure, are intended to be included within the scope of the present invention.

Preferred compounds of formula (1) are those in which R is hydrogen, acetyl or succinyl; $R_1$ is methyl or tertiarybutyl; $R_2$ and $R_3$ are each independently hydrogen, methyl or tertiarybutyl; $R_4$ is hydrogen or methyl; $R_6$ is methyl; A is methylene; and $R_5$ and $R_7$ are each independently methyl or —$(CH_2)_n$—(Ar) where n is 0 or 1 and Ar is phenyl unsubstituted or substituted with one to three substituents selected from the group consisting of hydroxy, methoxy, ethoxy, halogen, trifluoromethyl, $C_1$–$C_6$ alkyl, or —$NR_8R_9$, wherein $R_8$ and $R_9$ are each independently hydrogen or methyl. More preferred are the compounds:

2,6-Di-t-butyl-4-[(diphenylmethylsilyl)methyloxy]phenol
2,6-Di-t-butyl-4-[(4-N,N-dimethylaminophenyldimethylsilyl) methyloxy]phenol
2,6-Di-t-butyl-4-[(dimethyl-4-trifluoromethylphenylsilyl) methyloxy]phenol
2,6-Di-t-butyl-4-[(dimethyl-3-trifluoromethylphenylsilyl) methyloxy]phenol
2-t-Butyl-4-[(dimethylphenylsilyl)methyloxy]phenol
2,6-Di-t-butyl-4-[(dimethylphenylsilyl)methyloxy]phenol succinic acid ester
2-t-Butyl-4-[(dimethylphenylsilyl)methyloxy]phenol succinic acid ester
2,6-Di-t-butyl-4-[(dimethylphenylsilyl)methylthio]phenol succinic acid ester
2,6-Di-t-butyl-4-[(trimethylsilyl)methylthio]phenol succinic acid ester
2-t-Butyl-4-[(dimethylphenylsilyl)methyloxy]phenol acetic acid ester
2,6-Di-t-butyl-4-[(dimethylphenylsilyl)methyloxy]phenol acetic acid ester
2,3,6-Trimethyl-4-[(dimethylphenylsilyl)methyloxy]phenol acetic acid ester
2,5-Di-t-butyl-4-[(dimethylphenylsilyl)methyloxy]phenol
2,5-Di-t-butyl-4-[(dimethylphenylsilyl)methyloxy]phenol acetic acid ester
2-t-Butyl-4-[(dimethylphenylsilyl)methylthio]phenol
2,3,6-Trimethyl-4-[(dimethylphenylsdilyl)methloxy]phenol
2,3,5-Trimethyl-4-[(dimethylphenylsilyl)methyloxy]phenol
2-t-Butyl-4-[(dimethyl-p-methoxylphenylsilyl)methyloxy] phenol
2,5-Di-t-butyl-4-[(diphenylmethylsilyl)methyloxy]phenol
2,6-Di-t-butyl-4-[(diphenylmethylsilyl)methyloxy]phenol
2,6-Di-t-butyl-4-[(methyl-di-p-methoxyphenylsilyl)methyloxy]phenol
2,6-Di-t-butyl-4-[(dimethyl-p-methoxybenzylsilyl)methyloxy]phenol and
2-t-butyl-4-[(dimethylbenzylsilyl)methyloxy]phenol.

As used herein, the term "patient" refers to a warm-blooded animal or mammal which is in need of treatment for a chronic inflammatory disease, atherosclerosis, hypercholesterolemia or which is in need of inhibiting cytokine-induced expression of vascular cell adhesion molecule-1 and/or intercellular adhesion molecule-1. It is understood that guinea pigs, dogs, cats, rats, mice, hamsters, rabbits and primates, including humans, are examples of patients within the scope of the meaning of the term.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

An effective antiatherosclerotic amount of a compound of formula (1) is an amount which is effective in inhibiting the development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of atherosclerosis. It is further understood and appreciated by those of ordinary skill in the art that successful treatment for atherosclerosis can include prophylaxis in preventing atherosclerotic lesion or plaque formation.

Peroxidation of LDL lipid, such as the unsaturated fatty acid portions of LDL cholesteryl esters and phospholipids, is known to facilitate the deposition of cholesterol in macrophages which subsequently are deposited in the vessel wall and are transformed into foam cells. The identification of those patients who are in need of inhibition of peroxidation of LDL lipid is well within the ability and knowledge of one of ordinary skill in the art. For example, those individuals who are in need of treatment for atherosclerosis as defined hereinabove, are also patients who are in need of inhibition of peroxidation of LDL lipid. An effective antioxidant amount of a compound of formula (1) is an amount which is effective in inhibiting the peroxidation of LDL lipid in a patient's blood.

Hypercholesterolemia is a disease state characterized by levels of serum cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by use of clinical tests, physical examination and medical/family history, those patients who are suffering from hypercholesterolemia and those who are at risk of developing hypercholesterolemia and thus readily determine if an individual is a patient in need of hypercholesterolemia.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: asthma, chronic inflammation, rheumatoid arthritis, autoimmune diabetes, transplant rejection and tumor angiogenesis. A "therapeutically effective amount" of a compound of formula (1) is an amount which is effective, upon single or multiple dose administration to the patient, in providing relief of symptoms associated with chronic inflammatory diseases. An "effective vascular cell adhesion molecule-1 and/or intercellular cell adhesion molecule-1 inhibiting amount" of a compound of formula (1) is an amount which is effective, upon single or multiple dose administration to the patient, in providing relief of symptoms associated with vascular cell adhesion molecule-1 and/or intercellular adhesion molecule-1 mediated conditions.

As used herein, "relief of symptoms" of a chronic inflammatory disease or vascular cell adhesion molecule-1 mediated conditions refers to decrease in severity over that expected in the absence of treatment and does not necessarily indicate a total elimination or cure of the disease. Relief of symptoms is also intended to include prophylaxis.

In determining the therapeutically effective amount or dose, the effective antioxidant amount or dose, the plasma cholesterol lowering amount or dose, the effective antiatherosclerotic amount or dose or the effective VCAM-1 and/or ICAM-1 inhibiting amount of a compound of formula (1), a number of factors are considered by the attending diagnostician, including, but not limited to: the species of the mammal; its size, age, and general health; the specific disease involved; the degree of or involvment or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount, an effective antioxidant amount, a plasma cholesterol lowering amount, an effective antiatherosclerotic amount or an effective VCAM-1 and/or ICAM-1 inhibiting amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

The compounds of this invention are inhibitors of VCAM-1 and/or ICAM-1 expression. It is believed that the compounds of this invention exert their inhibitory effect through inhibition of VCAM-1 and/or ICAM-1 upregulation by cytokines and thereby prevent or provide relief of symptoms for chronic inflammatory diseases including asthma, chronic inflammation, rheumatoid arthritis, autoimmune diabetes, and the like; atherosclerosis and hypercholesterolemia. However, it is understood that the present invention is not limited by any particular theory or proposed mechanism to explain its effectiveness in an end-use application.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more-of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (1): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose.

The parenteral preparation can be enclosed in ampules, disposable syringes or multiple dose vials made of glass or plastic.

EXAMPLE 29

Cell Surface ELISA for VCAM-1/ICAM-1

Proliferating human umbilical vein endothelial cells (HUVEC) or human aortic smooth muscle cells (HASMC) from Clonetics (San Diego, Calif.) were plated onto 96-well plates in 100 μL medium per well at 20,000 cells per cm$^2$. The cultures were maintained in growth medium (EGM or SMGM2, Clonetics, San Diego, Calif.) for two days prior to addition of cytokines or drugs. Cytokines plus or minus compounds were added for 20 to 24 hours prior to analysis for adhesion molecule levels. Tumor necrosis factor (Genzyme, Cambridge, Mass.) was added to cultures at 500–1000 units/mL. Interleukin-4 (GIBCO-BRL, Gaithersburg, Md.) was added to cultures at 100–200 pg/mL. (Additions were made by transferring 100 [μL of cytokines plus compounds serially diluted on a separate 96-well plate into the plates containing cells. The medium on the cultures was not exchanged prior to addition of effectors). The culture medium was removed, and the monolayers were washed twice with Hanks buffered saline solution (HBSS) at room temperature. The primary antibody (anti-human VCAM-1 from Upstate Biotechnology, Inc., Lake Placid, N.Y. or anti-human ICAM-1 from Immunotech, Inc., Westbrook, Me.) was added to each well (1 μg/mL in HBSS plus 5% newborn calf serum, GIBCO-BRL, Gaithersburg, Md.) and incubated at 37° C. for 1 hr. The wells were washed twice with HBSS, then 100 μL of a 1/1000 dilution of goat anti-mouse IgG conjugated to horse radish peroxidase (BioRad, Hercules, Calif.) in HBSS plus 5% newborn calf serum was added to each well and incubated for 1 hr at 37° C. The wells were washed three times with HBSS, then 100 μL of TMB substrate (BioRad, Hercules, Calif.) was added to each well. The reaction was stopped after blue color developed by addition of 50 μL of 1N $H_2SO_4$. Absorbance is measured at 450 nm with a plate reader. $IC_{50}$ values were determined from curves of absorbance values obtained from serial dilutions of compounds (dissolved in dimethyl sulfoxide).

The $IC_{50}$ value is defined as the drug concentration that inhibits the cytokine-induced adhesion molecule expression by 50%. Maximal values for adhesion molecule expression in cytokine-induced cultures was subtracted from the basal level of adhesion molecule expression (minus cytokines) in the cultures to determine the level of induction. VCAM-1 was typically induced about 5–7 fold. ICAM-1 was typically induced 5–10 fold. Each drug concentration was tested in quadruplicate wells. Single point tests of compounds at 50 μM were assayed as described for $IC_{50}$ determinations, except that the data represent the level of inhibition without correction for basal expression. (Basal adhesion molecule expression was 10–20% of the total induced expression). Table 1 summarizes the ability of various compounds of this invention to inhibit VCAM-1 using human aortic smooth muscle cells (HASMC). In these experiments, the cells were coincubated with interleukin-4 and the compounds listed about 20 hr before assaying cell surface VCAM-1 levels. Each column represents a separate experiment.

TABLE 1

Inhibition of VCAM-1 in Human Aortic Smooth Muscle Cells (HASMC)

| Cmpd. No. (MDL No.) | HSMC-1 (% inh. 50 μm) | HSMC-2 (% inh. 50 μm) | HSMC-3 (% inh. 50 μm) | VCAM-1 (Avg.) |
|---|---|---|---|---|
| 104,599 | 50.1 | 38.0 | 49.0 | 45.7 |
| 104,556 | 54.1 | 58.0 | 58.0 | 56.7 |
| 105,975 | (11.6) | 20.0 | 51.0 | 19.8 |
| 103,491 | N.T.* | 57.0 | 49.0 | 53.0 |
| 103,076 | 30.6 | 55.0 | 46.0 | 43.9 |
| 103,141 | 13.7 | 47.0 | 33.0 | 31.2 |
| 104,863 | 56.5 | 52.0 | 56.0 | 54.8 |
| 103,377 | N.T. | 45.0 | 46.0 | 45.5 |
| 105,443 | 11.4 | 44.0 | 22.0 | 25.8 |
| 105,314 | 8.7 | 38.0 | 38.0 | 28.2 |
| 103,653 | 63.1 | 54.0 | 52.0 | 56.4 |

*N.T. = Not tested

Table 2 summarizes the ability of various compounds of this invention to selectively inhibit VCAM-1 or to inhibit both VCAM-1 and ICAM-1 using proliferating human umbilical vein endothelial cells (HUVEC). In these experiments, the cells were coincubated with tumor necrosis factor-alpha along with the indicated compounds about 20 to 24 hr before assaying cell surface adhesion molecule expression.

TABLE 2

Inhibition of VCAM-1 and/or ICAM-1 in Human Umbilical Vein Endothelial Cells (HUVEC)

| Cmpd. No. (MDL No.) | VCAM-1 (% inh. 50 μM)* | ICAM-1 (% inh. 50 μM) @ |
|---|---|---|
| 104,599 | 12.3 | (9.5) |
| 104,556 | 33.3 | 1.5 |
| 105,975 | 6.3 | 2.5 |
| 103,491 | 12.0 | 80 |
| 103,076 | 7.3 | 76 |
| 103,141 | 1.3 | 79.5 |
| 104,863 | 44.3 | 53 |
| 103,377 | 18.3 | (5.0) |
| 105,443 | 3.0 | 73.0 |
| 105,314 | 10.7 | 75.5 |
| 103,653 | 37.7 | 78.5 |

*Average of three runs
@Average of two runs, numbers in parentheses represent negative values In vivo activity of these compounds can also be assessed in other models of inflammation predicted to involve elevated VCAM-1 levels. One such model for respiratory diseases, such as asthma, is an ovalbumin-sensitized model. Kung, T. T. et al., *Int. Arch. Allergy Immunol.* 105, 83–90 (1994). This model of pulmonary inflammation is IgE mediated and involves eosinophillia (as does the asthmatic human). The bronchial alveolar lavage (BAL) fluid obtained from experimental animals can be assessed for a number of parameters, including soluble adhesion molecule expression and leukocyte accumulation. Adhesion molecule expression can be assessed by immunohistochemistry within the tissues, especially the lung, of experimental animals. The effect of the claimed compounds, such as MDL 29,353, should be to suppress the upregulation of VCAM-1 expression and inhibit eosinophil accumulation in the BAL fluid. The inhibitors could be tested in a rat model of adjuvant arthritis, which has been previously shown to respond to anti-ICAM-1 monoclonal antibodies. Iigo, Y. et al., *J. Immunol.* 147, 4167–4171 (1991). In this model, adhesion molecule expression would be assessed in the limbs (joints) of experimental animals. For autoimmune diabetes, one could test the compounds for their ability to delay the onset or prevent adoptive transfer of disease in the NOD mouse model. Heinke, E. W. et al., *Diabetes* 42, 1721–1730 (1993); Baron, J. L. et al., *J. Clin. Invest.* 93, 1700–1708 (1994). Furthermore, one can monitor the level of VCAM-1 expression in the tissues (e.g. pancreas) as well as monitor the development of diabetes in the experimental animal. Therapeutic potential for transplant rejection can be assessed by monitoring cardiac allograft survival (Balb/c hearts transplanted into C3H/He recipients. Isobe, M. et al., *J. Immunol.* 153, 5810–5818 (1994). In vivo administration of anti-VCAM-1 and anti-VLA-4 monoclonal antibodies induces immunosuppression to cardiac allografts and soluble antigens in this mouse model. Compound effects on tumor metastasis and angiogenesis can be evaluated in a number of models. These can include the B16 (murine) and M24met (human) melanoma models for experimental metastasis. Fidler, I. J., *Cancer Res.* 35, 218–224 (1975); Meuller, B. M. et al., *Cancer Res.* 51, 2193–2198. Activity of the compounds can be assessed by their effect on the number of lung metastases which develop, as well as their effect on VCAM-1 expression in the lung as described above for the mouse respiratory model. A model for evaluating antiangiogenic compounds which can be used to test the compounds involves monitoring the vascular response to a mixture of angiogenic factors mixed with basement membrane proteins injected subcutaneously in mice. Passaniti, A. et al., *Lab. Invest.* 67, 519–528 (1992). Angiogenesis is scored by the number of vessels recruited into the matrigel and by the hemoglobin content of the gels. Adhesion molecule expression and accumulation of leukocyte can be determined by immunohistochemical methods as in all of the above examples.

EXAMPLE 30

Hypochloesterolemic and Antioxidant Effects of Compounds of Formula (1) in Chloleterol-Fed Female New Zealand White Rabbits A. Experimental Protocol Five independent experiments were performed in the following manner. Each study had a control group and 1–5 groups treated with MDL compound (N=5 per group). Female New Zealand White rabbits (Hazelton, ~2.0–2.3 kg) were fed 0.2% cholesterol enriched rabbit chow (Purina #5322) with or without 0.4% MDL compound (except, MDL 108,804 at 0.26% and MDL 103,491 repeated at 0.6%). The MDL compounds were solubilized in 100% ethanol. MDL 108,208 was not soluble in 100% ethanol, but it was soluble in diethyl ether:ethanol (3:2 by volume). The chow was sprayed with the MDL mixtures and allowed to dry overnight in a chemical fume hood. Control chow was sprayed with ethanol. Rabbits were fed 100 grams food per day for 7 days (0.6% MDL 103,491 were fed for 14 days); water was available ad libitum. On day 7, rabbits (fasted overnight) were bled (~2 mL) from marginal ear vein; 0.6% MDL 103,491 treated rabbits were tested on day 14. They were euthanized by carbon dioxide overdose. The total body and liver weights were recorded in grams. Food consumption was recorded as grams•day$^{-1}$•rabbit$^{-1}$. Aliquots of fresh serum were used for clinical chemistries, lipoprotein cholesterol determination, thiobarbituric acid reactive substances (TBARS) and compound and metabolite concentrations in serum. Livers (~5 gram aliquots) were frozen at −20° C. for compound and metabolite concentration determination at a later time.

B. Clinical Chemistries

Blood was allowed to clot at room temperature for 30 minutes. Serum was obtained after centrifugation for 10 min at 5° C. at 3000 rpm in a Beckman GPKR centrifuge with a GH rotor. Fresh serum was analyzed by a COBAS MIRA autoanalyzer (Roche Diagnostics) using Roche diagnostic reagents for total cholesterol (CHOL, kit #44334) and triglyceride (TG, kit #44120). Cholesterol and triglycerides were calculated as mg/dL.

C. TBARS Assay

TBARS are a qualitative indication of the oxidation of lipids in a sample. In this assay the oxidation of serum lipids is initiated with $CuSO_4$, resulting in the formation of aldehydes, such as malondialdehyde (MDA). Upon incubation with thiobarbituric acid, the absorbance of the aldehydes can be detected at 530–540 nm. TBARS values which are lower than control serum values indicate the relative ability of a compound to inhibit the oxidation. TBARS were measured as follows: 50 μL of serum were mixed with 50 μL of 0.9% saline and 400 μL of a 5 mM $CuSO_4$ solution and incubated at 37° C. for 5 hr. The reactions were stopped by addition of 1.0 mL of 20% trichloroacetic acid. Then 1.0 mL of 0.67% thiobarbituric acid in 0.05N sodium hydroxide was added, mixed, and the samples incubated for 30 min at 90° C. Samples were centrifuged briefly to pellet undissolved material, and the supernatants were transferred to a 96-well microtiter plate. Absorbances were measured at 540 nm using a Biotek model EL311 microplate reader. The nmoles of MDA produced were calculated from a standard curve of 0 to 10 nmoles of MDA prepared from malonaldehyde bis(dimethylacetal). Serum samples from treated rabbits were compared to serum samples from control rabbits that received no MDL compound.

D. HPLC Quantitation of Compound and Metabolite Concentration in Serum and Liver Serum and liver concentrations of parent compounds and the metabolites, bisphenol and diphenoquinone, were determined by reverse phase HPLC using a Waters 990 Powerline system. Livers (1 gram) were homogenized with 5.0 mL PBS, pH 7.4, using a Polytron tissue homogenizer at setting 5 for 20–30 seconds. Serum or liver homogenates were extracted as follows: 100 µL of either serum or homogenate were added to 2.0 mL diethyl ether:ethanol (3:1) while vortexing the tube. The sample tubes were capped and centrifuged for 10 min at 5° C. at 3500 rpm in a Beckman GPKR centrifuge with a GH 3.7 rotor. The supernatants were transferred to clean tubes and dried under $N_2$. Samples were reconstituted with 200 µL of acetonitrile:hexane:0.1M ammonium acetate (90:6.5:3.5, by vol.). Then, 100 µL were injected onto a Waters Deltapak C18–300 Å column, and eluted with an 83% acetonitrile:17% water mobile phase at a flow rate of 1.5 mL/min. Absrobances at the wavelengths of 240, 254, and 420 nm were recorded. Compound concentrations were calculated from known quantities of authentic parent compounds after correction for recovery; the range of recovery from spiked samples was 40 to 100%. The lowest detectable limit for this class of compounds was ~0.5 µg/mL. Concentrations were calculated as µg/mL of serum and µg/g of liver.

E. HPLC Separation and Quantitation of Lipoprotein Subfraction Cholesterol Levels Lipoprotein fractions (very low density lipoprotein, VLDL, low density lipoprotein, LDL and high density lipoprotein, HDL) were separated on a Sepharose 6HR column (1×30 cm, Pharmacia) attached to a Waters Powerline HPLC system. Fifty µL of serum were injected onto the column and eluted with phosphate buffered saline, pH 7.4, at a flow rate of 0.5 mL/min. Cholesterol reagent (Roche Diagnostics, kit #44334, diluted with 20 mL water and then with 20 mL of 0.9% saline) was added at 0.2 mL/min to the post column eluant and incubated in a knitted PFTE Kratos reaction coil (Applied Biosystems) at 37° C. for 5 min. Absorbance was measured at 500 nm. The lipoprotein subfractions were quantitated as follows:

$$(\text{total serum cholesterol}) \times \frac{\text{\% area under the curve}}{\text{for each subfraction}}$$

Tables 3 and 4 below present summary data from the individual experiments of this testing procedure.

TABLE 3

Hypochloesterolemic and Antioxidant Effects of Compounds of Formula (1) in Choleterol-Fed Female New Zealand White Rabbits as a Percent of Conrol

| MDL# | Diet % | food | body wt. | lw/bw | chol tot. | LDL | HDL | TRIG | TBARS |
|---|---|---|---|---|---|---|---|---|---|
| 103,491 | 0.4 | 100% | 100% | 89% | 85% | 81% | 103% | 134% | 32% |
| 103,491 | 0.6 | 80% | 95% | 96% | 139% | ND* | ND | 216% | 18% |
| 104,556 | 0.4 | 100% | 97% | 96% | 47% | 53% | 116% | 81% | 70% |
| 104,599 | 0.4 | 98% | 99% | 86% | 76% | 71% | 105% | 64% | 79% |
| 104,962 | 0.4 | 69% | 97% | 71% | 118% | 105% | 163% | 159% | 19% |
| 105,443 | 0.4 | 100% | 101% | 90% | 98% | 97% | 115% | 127% | 42% |
| 105,975 | 0.4 | 100% | 101% | 108% | 69% | 77% | 76% | 143% | 68% |
| 106,834 | 0.4 | 99% | 99% | 94% | 67% | 89% | 61% | 98% | 70% |
| 107,917 | 0.4 | 100% | 99% | 106% | 151% | 165% | 86% | 129% | 68% |
| 108,208 | 0.4 | 100% | 97% | 103% | 109% | 117% | 97% | 107% | 89% |
| 108,804 | 0.26 | 100% | 101% | 96% | 91% | 82% | 109% | 143% | 49% |

*ND = not determined
N = 5 rabbits/group; fasted overnight
Rabbits were fed × 7 days (except MDL 103,491 at 0.6% was for 14 days).
Diet % = (weight MDL compound/weight food) × (100)
The data in Table 3 were normalized as follows: % Control = (Mean, treated group/Mean, control group) × (100)
Food = grams eaten per day per rabbit
Body wt. = weight in grams
LW/BW = (liver weight/body weight in grams)
CHOL = total cholesterol mg/dl
LDL = Low Density lipoprotein cholesterol mg/dl
HDL = High Density lipoprotein cholesterol mg/dl
TRIG = triglycerides, mg/dl
TBARS = thiobarbituric acid reactive substances, expressed as nmole MDA

TABLE 4

Drug and Metabolite Concentration in Rabbit Serum and Liver

| | | Liver | | | Liver | | |
|---|---|---|---|---|---|---|---|
| MDL # | Diet % | Parent | Bis | Quin | Parent | Bis | Quin |
| 103,491 | 0.4 | 0 | 0 | 0 | 0 | 0 | 0 |
| 103,491 | 0.6 | 0 | 0 | 0 | 0 | 0 | 0 |
| 104,556 | 0.4 | 4.9 | 0 | 0 | 7.9 | 0 | 0 |
| 104,599 | 0.4 | 14.8 | 0 | 0 | 47.2 | 0 | 0 |
| 104,962 | 0.4 | 3.8 | 0 | 0 | 3.6 | 0 | 0 |
| 105,443 | 0.4 | 0 | 0 | 0 | 0 | 0 | 0 |
| 105,975 | 0.4 | 13.8 | 0 | 0 | 54.6 | 0 | 0 |
| 106,834 | 0.4 | 2.9 | 0 | 0 | 9.1 | 0 | 0 |
| 107,917 | 0.4 | 0 | 0 | 0 | 0 | 0 | 0 |
| 108,208 | 0.4 | 0 | 0 | 0 | 0 | 0 | 0 |
| 108,804 | 0.26 | 0 | 0 | 0 | 0 | 0 | 0 |

N = 5 rabbits/group; fasted overnight
Rabbits were fed × 7 days (except MDL 103,491 at 0.6% was for 14 days).
Diet % = (weight MDL compound/weight food) × (100)
The data in Table 4 are presented as Means (N = 5) and have not been normalized to control values.
Serum Parent = parent compound concentration as µg/ml of serum
Serum Bis = bisphenol concentration as µg/ml of serum
Serum Quin = diphenoquinone concentration as µg/g serum
Liver Parent = parent compound concentration as µg/g liver
Liver Bis = bisphenol concentration as µg/g liver
Liver Quin = diphenoquinone concentration as µg/g liver Measurement of Antioxidant Activity and Bioavailability of Compound of Formula (1) By In Vivo Screening in Male Sprague-Dawley Rats A. Experimental Protocol A typical experiment consisted of 4–6 groups of rats (N=5 per group) with 1 group being a control which received no MDL compound and the other groups being treated with 0.3% MDL compound. Some of the compounds were either repeated at 0.3% or evaluated again at the lower dose of 0.1%. Male Sprague-Dawley rats, 50–100 g, (Harlan Laboratories, Indianapolis, Ind.) were housed in groups of 5, fed ad libitum water and Purina Rodent chow (#5002) with or without MDL compound as a dietary admixture for 4 days. Dietary admixtures (0.3%) were made by mixing 1.2 grams of an MDL compound with 400 grams of Purina rodent chow (#5002). The MDL compound was mixed with approximately 50 grams of food using a mortar and pestle. This was added to the remainder of the food and mixed for 3 hours on a rotary mixer. In the morning of day 5, non-fasted rats were anesthetized with carbon dioxide, and blood was collected by cardiac puncture. Rats were sacrificed by cervical dislocation. Body weights and liver weights were recorded in grams. Food consumption was recorded as grams•day$^{-1}$•rat$^{-1}$. Deaths were recorded as mortality. Aliquots of fresh serum were used for clinical chemistries, thiobarbituric acid reactive substances (TBARS) and conjugated diene measurements. Aliquots of serum (~0.5mL) and whole livers were frozen at –20° C. for compound and metabolite concentration determination at a later time.

B. Clinical Chemistries

Blood was allowed to clot at room temperature for 30 minutes. Serum was obtained after centrifugation for 10 min at 4° C. at 3000 rpm in a Beckman J-6M/E centrifuge with a JS-4.2 rotor. Fresh serum was analyzed by a COBAS MIRA S autoanalyzer (Roche Diagnostics) using Roche diagnostic reagents for the following clinical chemistry measurements: alkaline phosphatase (ALP, kit #44553), alanine transaminase (ALT, kit #42375), aspartate aminotransferase (AST, kit #42381), total cholesterol (CHOL, kit #44334), triglyceride (TG, kit #44120), and glucose (GLU, kit #44558). ALP, ALT, and AST were calculated as units/L. Cholesterol, triglycerides, and glucose were calculated as mg/dL.

C. HPLC—Quantitation of Compound of Metabolite Concentration in Serum and Liver

Serum and liver concentrations of parent compound and the metabolites, bisphenol and diphenoquinone, were determined by reverse phase HPLC using a Waters 990 Powerline system. Livers (1 gram samples) were homogenized with 5.0 mL PBS, pH 7.4, using a Polytron tissue homogenizer at setting 5 for 20–30 seconds. Serum or liver homogenates were extracted as follows: 100μL of either serum or homogenate were added to 2.0 mL diethyl ether:ethanol (3:1) while vortexing the tube. The sample tubes were capped and centrifuged for 10 min at 5° C. at 3500 rpm in a Beckman GPKR centrifuge with a GH 3.7 rotor. The supernatants were transferred to clean tubes and dried under $N_2$. Samples were reconstituted with 200 μL of acetonitrile:hexane:0.1M ammonium acetate (90:6.5:3.5, by vol.). Then, 100 μL were injected onto a Waters Deltapak C18-300 Å column, and eluted with an 83% acetonitrile:17% water mobile phase at a flow rate of 1.5 mL/min. Absorbances at the wavelengths of 240, 254, and 420 nm were recorded. Compound concentrations were calculated from known quantities of authentic parent compounds after correction for recovery; the range of recovery from spiked samples was 40 to 100%. The lowest detectable limit for this class of compounds was ~0.5 μg/mL. Concentrations were calculated as μg/mL. Concentrations were calculated as μg/mL of serum and μg/g of liver.

D. Thiobarbituric Acid Reactive Substances (TBARS) Assay

In this assay the oxidation of serum lipids is initiated with $CuSO_4$, resulting in the formation of aldehydes, such as malondialdehyde (MDA). Upon incubation with thiobarbituric acid, the absorbance of the aldehydes can be detected at 530–540 nm. As stated in the previous example, TBARS values which are lower than control serum values indicate the relative ability of a test compound to inhibit the oxidation of lipids in a sample. TBARS were measured as follows: 100 μL of serum were mixed with 400 μL of a 5 mmol $CuSO_4$ solution and incubated at 37° C. for 3 hr. The reactions were stopped by addition of 1.0 mL of 20% trichloroacetic acid. Then 1.0 mL of 0.67% thiobarbituric acid in 0.05N sodium hydroxide was added, mixed, and the samples incubated for 30 min at 90° C. Samples were centrifuged briefly to pellet undissolved material, and the supernatants were transferred to a 96-well microtiter plate. Absorbances were measured at 540 nm using a Biotek model EL311 microplate reader. The nmoles of MDA produced were calculated from a standard curve of 0 to 10 nmoles of MDA prepared from malonaldehyde bis(dimethylacetal). Serum samples from treated rats were compared to serum samples from control rats that received no MDL compound.

E. Conjugated Diene Determination

Conjugated diene lag phase is another indicator of the oxidation of lipids. Lipids exposed to $Cu^{++}$ form conjugated dienes that absorb ultraviolet light in the range of 230 to 235 nm. The lag phase of diene formation gives an indication of the amount of oxidation of the lipids. A lag phase longer than control samples indicate inhibition of the oxidation. Conjugated diene lay phase was determined using a Varian DMS200 spectrophotometer (fitted with a constant temperature, 5 cuvette sample changer) at 30° C. Twenty (20) μL of pooled serum were added to cuvettes containing 3.0 mL phosphate buffered saline, pH 7.5, and mixed. The absorbances of all cuvettes were measured, and the instrument baseline was set to zero using the lowest absorbing sample. Next, 100 μL of 1 mmol $CuSO_4$ were added and immediately mixed. The absorbance of each cuvette was recorded at 2 min intervals for a period of 840 min. The data were captured and transferred to a Microsoft EXCEL® spreadsheet where the curves were smoothed and differentials obtained. Lag times were determined mathematically as minutes. Serum samples were pooled (N=5); data presented are the mean values of 2 determinations. Serum samples from treated rats were compared to serum samples from control rats that received no MDL compound.

Tables 5, 6 and 7 below present summary data from the individual experiments of this testing procedure. Table 5 presents measurements of the serum chemistries in the male Sprague-Dawley rats, Table 6 presents the animal parameters and Table 7 provides the drug or metabolite concentrations in both the serum and the liver.

TABLE 5

Antioxidant Effects of Compounds of Formula (1) in Male Sprague-Dawley Rats as a Percent of Control

| MDL No. | Diet % | ALP | AST | ALT | CHOL | GLUC | TRIG | TBARS | CONJ. DIENE (min.) |
|---|---|---|---|---|---|---|---|---|---|
| 103,076 | 0.3 | 201% | 99% | 132% | 114% | 99% | 77% | 107% | ND* |
| 103,141 | 0.3 | 147% | 120% | 126% | 119% | 107% | 47% | 113% | ND |
| 103,157 | 0.3 | 144% | 92% | 133% | 112% | 100% | 82% | 94% | 50 |
| 103,377 | 0.3 | 147% | 149% | 145% | 93% | 102% | 85% | 71% | ND |
| 103,491 | 0.3 | 80% | 114% | 127% | 146% | 94% | 131% | 34% | ND |
| 103,491 | 0.1 | 116% | 94% | 133% | 112% | 101% | 92% | 70% | 168 |
| 104,399 | 0.3 | 91% | 102% | 107% | 130% | 88% | 168% | 41% | 395 |
| 104,556 | 0.3 | 112% | 101% | 106% | 119% | 113% | 95% | 34% | ND |
| 104,556 | 0.1 | 112% | 107% | 125% | 96% | 102% | 74% | 61% | 200 |
| 104,571 | 0.3 | 103% | 103% | 109% | 108% | 96% | 119% | 58% | ND |
| 104,599 | 0.3 | 110% | 76% | 91% | 94% | 111% | 100% | 34% | ND |
| 104,962 | 0.3 | 130% | 109% | 112% | 99% | 91% | 74% | 25% | 320 |
| 105,314 | 0.3 | 154% | 76% | 113% | 110% | 115% | 78% | 85% | ND |
| 105,443 | 0.1 | 101% | 94% | 116% | 111% | 106% | 111% | 78% | 151 |
| 105,443 | 0.3 | 90% | 171% | 156% | 131% | 98% | 126% | 14% | ND |
| 105,726 | 0.3 | 118% | 112% | 113% | 104% | 105% | 75% | 48% | ND |
| 105,975 | 0.3 | 105% | 122% | 106% | 122% | 106% | 107% | 24% | ND |
| 105,975 | 0.1 | 112% | 89% | 96% | 98% | 110% | 108% | 67% | ND |
| 106,290 | 0.3 | 118% | 84% | 89% | 153% | 109% | 75% | 17% | 372 |
| 106,834 | 0.3 | 69% | 122% | 141% | 150% | 95% | 83% | 31% | 492 |
| 108,701 | 0.3 | 96% | 96% | 111% | 99% | 112% | 58% | 62% | 274 |

*ND = not determined
N = 5 rats per group
Diet % = (weight MDL compound/weight food) × (100)
Conj. Diene = conjugated diene lag phase in minutes (mean of 2 determinations of pooled samples, N = 5)
The data in Table 5, except for conjugated dienes and diet percent, have been normalized as follows: Control = (Mean, treated group/Mean, control group) × (100)
ALP = alkaline phosphatase, U/mL
AST = aspartate aminotransferase, U/mL
ALT = alanine aminotransferase, U/mL
CHOL = total cholesterol, mg/dl
TG = triglycerides, mg/dl
GLU = glucose, mg/dl
TBARS = thiobarbituric acid reactive substances, expressed as nmoles MDA

TABLE 6

Animal Parameters as a Percent of Control

| MDL No. | Diet % | food | body wt. | lw/bw | mortality |
|---|---|---|---|---|---|
| 103,076 | 0.3 | 93% | 105% | 110% | 0% |
| 103,141 | 0.3 | 87% | 91% | 96% | 0% |
| 103,157 | 0.3 | 96% | 96% | 120% | 0% |
| 103,377 | 0.3 | 82% | 97% | 105% | 0% |
| 103,491 | 0.3 | 89% | 100% | 130% | 0% |
| 103,491 | 0.1 | 92% | 95% | 106% | 0% |
| 104,399 | 0.3 | 90% | 101% | 118% | 0% |
| 104,556 | 0.3 | 68% | 87% | 120% | 0% |
| 104,556 | 0.1 | 102% | 103% | 106% | 0% |
| 104,571 | 0.3 | 108% | 97% | 123% | 0% |
| 104,599 | 0.3 | 103% | 93% | 107% | 0% |
| 104,962 | 0.3 | 74% | 95% | 103% | 0% |
| 105,314 | 0.3 | 109% | 111% | 118% | 0% |
| 105,443 | 0.1 | 100% | 101% | 110% | 0% |
| 105,443 | 0.3 | 84% | 95% | 118% | 0% |
| 105,726 | 0.3 | 112% | 105% | 120% | 0% |
| 105,975 | 0.3 | 98% | 100% | 113% | 0% |
| 105,975 | 0.1 | 106% | 98% | 105% | 0% |
| 106,290 | 0.3 | 108% | 95% | 104% | 0% |
| 106,834 | 0.3 | 91% | 95% | 132% | 0% |
| 108,701 | 0.3 | 90% | 97% | 119% | 0% |

N = 5 rats/group
Diet % = (weight MDL compound/weight food) × (100)
The data in Table 6 have been normalized according to the formula presented in Table 5.
Food = grams eaten per day per rat
Body weight = weight in grams
LW/BW = (liver weight/body weight in grams)
Mortality = deaths per group

TABLE 7

Drug and Metabolite Concentration in Rat Serum and Liver

| MDL No. | Diet % | Serum Parent | Serum Bis | Serum Quin | Parent | Bis | Quin |
|---|---|---|---|---|---|---|---|
| 103,076 | 0.3 | 0 | 0 | 0 | 0 | 0 | 0 |
| 103,141 | 0.3 | 0 | 0 | 0 | 0 | 0 | 0 |
| 103,157 | 0.3 | 0 | 0 | 0 | 0 | 0 | 0 |
| 103,377 | 0.3 | 7.72* | 0 | 0 | 22.2** | 0 | 0 |
| 103,491 | 0.3 | 3 | 0 | 0 | 0 | 0 | 0 |
| 103,491 | 0.1 | 0 | 0 | 0 | 0 | 0 | 0 |
| 104,399 | 0.3 | 0 | 0 | 0 | 0 | 0 | 0 |
| 104,556 | 0.3 | 16.3 | 0 | 0 | 60.3 | 0 | 0 |
| 104,556 | 0.1 | 9.2 | 0 | 0 | 38.7 | 0 | 0 |
| 104,571 | 0.3 | 1.2 | 0 | 0 | 0.5 | 0 | 0 |
| 104,599 | 0.3 | 28.3 | 0 | 0 | 44.9 | 0 | 0 |
| 104,962 | 0.3 | 16.4 | 0 | 0 | 43.5 | 0 | 0 |
| 105,314 | 0.3 | 0.0 | 0 | 0 | 0.0 | 0 | 0 |
| 105,443 | 0.1 | 0 | 0 | 0 | 0 | 0 | 0 |
| 105,443 | 0.3 | 0.0† | 0 | 0 | 0 | 0 | 0 |
| 105,726 | 0.3 | 17 | 0 | 0 | 128.3 | 0 | 0 |
| 105,975 | 0.3 | 35.8 | 0 | 0 | 185.9 | 0 | 0 |
| 105,975 | 0.1 | 23.8 | 0 | 0 | 94.5 | 0 | 0 |
| 106,290 | 0.3 | 4.8‡ | 0 | 0 | 26.2‡‡ | 0 | 0 |
| 106,834 | 0.3 | 1.8 | 0 | 0 | 2.7 | 0 | 0 |
| 108,701 | 0.3 | 8 | 0 | 0 | 28.2 | 0 | 0 |

*In addition, 2.3 µg/mL of 2,6-di-t-butyl-4-[(dimethylphenyl-silyl)methyloxy]phenol was also observed.
**19.2 Kg/mg of 2,6-di-t-butyl-4-[(dimethylphenylsilyl)methyloxy]-phenol was also observed.
†3.8 µg/mL of MDL 103,491 was also observed.
‡This value represents the amount of MDL 104,962 observed.
‡‡This value represents the amount of MDL 104,962 observed.
The data in Table 7 are presented as Means (N = 5) and have not been normalized to control values.
Serum Parent = parent compound concentration as µg/ML of serum
Serum Bis = bisphenol concentration as µg/ml of serum
Serum Quin = diphenoquinone concentration as µg/g serum
Liver Parent = parent compound concentration as µg/g liver
Liver Bis = bisphenol concentration as µg/g liver
Liver Quin = diphenoquinone concentration as µg/g liver

EXAMPLE 32

Antiatherosclerotic Effects of Compounds of Formula (1) in Cholesterol-Fed Female New Zealand White Rabbits A. Experimental Protocol Conduct four independent experiments. Each experiment has a control group and 1–5 groups treated with MDL compound (N=5 per group). Feed Female New Zealand White Rabbits (Hazelton, ~2.0–2.3 kg) 1% cholesterol enriched rabbit chow (Purina #5322) with or without 0.4% of an MDL compound. Solubilize the MDL compound in 100% ethanol, spray on the chow, and dry overnight in a chemical fume hood. Alternatively, the MDL compounds can be incorporated into the rabbit food by Purina. Control chow is sprayed with ethanol. Feed rabbits 100 grams food per day for 70 days and allow water to be made available ad libitum. Rabbits (fasted overnight) are bled (~2mL) from a marginal ear vein periodically to monitor serum cholesterol levels. Euthanize rabbits on day 70 by carbon dioxide overdose. Record total body and liver weights in grams. Record food consumption as grams•day$^{-1}$. Use aliquots of fresh serum for clinical chemistries, lipoprotein cholesterol determination, thiobarbituric acid reactive substances (TBARS) and compound and metabolite concentrations is serum. Freeze livers (~5 gram aliquots) at −20° C. for compound and metabolite concentration determination at a later time.

Dissect aortas immediately after each rabbit is killed. Excise the aorta from the ascending arch to the iliac bifurcation after debridement of extraneous adipose tissue. Store aortas overnight in phosphate buffered saline, pH 7.4, at 4° C. until final debridement. Cut open aortas longitudinally and stain with Sudan IV. After staining, pin flat the aortas and quantitate the areas of sudanophilic lesions after capturing an image electronically.

B. Clinical Chemistries

Allow blood to clot at room temperature for 30 minutes. Obtain serum after centrifugation for 10 min at 5° C. at 3000 rpm in a Beckman GPKR centrifuge with a GH 3.7 rotor. Analyze fresh serum by a COBA MIRA S autoanalyzer (Roche Diagnostics) using Roche diagnostic reagents for total cholesterol (CHOL, kit #44334) and triglyceride (TG, kit #44120). Calculate cholesterol and triglycerides as mg/dL.

C. TBARS Assay

Initiate the oxidation of serum lipids with $CuSO_4$ to form aldehydes, such as malondialdehyde (MDA). Upon incubation with thiobarbituric acid, detect the absorbance of the aldehydes at 530–540 nm. Measure TBARS as follows: mix 50 µL of serum with 50 µL of 0.9% saline and 400 µL of a 5 mmol $CuSO_4$ solution and incubate at 37° C. for 5 hr. Stop the reactions by addition of 1.0 mL of 20% trichloroacetic acid. Add 1.0 mL of 0.67% thiobarbituric acid in 0.05N sodium hydroxide, mix and incubate the samples for 30 min at 90° C. Centrifuge the samples briefly to pellet undissolved material and transfer the supernatants to a 96-well microtiter plate. Measure absorbances at 540 nm using a Biotek model EL311 microplate reader. The nmoles of MDA produced are calculated form a standard curve of 0 to 10 nmoles of MDA prepared form malonaldehyde bis(dimethyacetal). Compare serum samples from treated rabbits to serum samples from control rabbits that received no MDL compound.

D. HPLC—Quantitation of Serum and Liver Compound and Metabolite Concentration

Determine the serum and liver concentrations of parent compounds and the metabolites, bisphenol and diphenoquinone, by reverse phase HPLC using a Waters 990 Powerline system. Homogenize livers (1 gram) with 5.0 mL PBS, pH 7.4, using a Polytron tissue homogenizer at setting 5 for 20–30 seconds. Extract serum or liver homogenates as follows: Add 100 µL of either serum or homogenate to 2.0 mL diethyl ether:ethanol (3:1) while vortexing the tube. Cap and centrifuge the sample tubes for 10 min at 5° C. at 3500 rpm in a Beckman GPKR centrifuge with a GH 3.7 rotor. Transfer the supernatants to clean tubes and dry under $N_2$. Reconstitute samples with 200 µL of acetonitrile:hexane:0.1 ammonium acetate (90:6.5:3.5, by vol.). Then, inject 100 µL onto a Waters Deltapak C18-300Å column, and elute with an 83% acetonitrile:17% water mobile phase at a flow rate of 1.5 mL/min. Record absorbances at the wavelengths of 240, 254, and 420 nm. Calculate compound concentrations from known quantities of authentic parent compounds after correction for recovery. Calculate concentrations as µg/mL or serum and µg/g of liver.

E. HPLC—Separation and Quantitation of Lipoprotein Subfraction Cholesterol Levels Separate lipoprotein fractions of VLDL, LDL and HDL on a Sepharose 6HR column (1×30 cm, Pharmacia) attached to a Waters Powerline HPLC system. Inject 50 µL of serum onto the column and elute with phosphate buffered saline, pH 7.4, at a flow rate of 0.5 mL/min. Add cholesterol reagent (Roche Diagnostics, kit #44334, diluted with 20 mL of water and then 20 mL of 0.9% saline) at 0.2 mL/min to the post column eluant and incubate in a knitted PFTE Kratos reaction coil (Applied Biosystems) at 37° C. for 5 min. Measure absorbance at 500 nm. Quantitate the lipoprotein subfractions as follows:

(total serum cholesterol) × (% area under the curve for each subfraction).

In addition, the compounds of formula (1) can be used as chemical antioxidant additives in organic materials normally subject to oxidative deterioration, such as, for example, rubber, plastics, fats, petroleum products and the like. In general, a preservative amount of a compound of formula (1), which is sufficient in concentration to inhibit oxidative deterioration of the material to be protected, is admixed with the material subject to oxidation. The preservative amount of a compound of formula (1) will generally vary from about 0.01% to about 1.0% by weight.

What is claimed is:

1. A compound of the formula

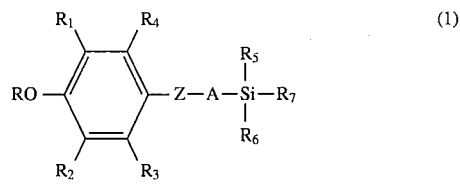

wherein $R_1$ and $R_6$ are each independently $C_1$–$C_6$ alkyl;

$R_2$, $R_3$ and $R_4$ are each independently hydrogen or $C_1$–$C_6$ alkyl;

R is hydrogen or —C(O)—$(CH_2)_m$—Q wherein Q is hydrogen or —COOH and m is an integer 1, 2, 3 or 4;

Z is a thio, oxy or methylene group;

A is a $C_1$–$C_4$ alkylene group;

$R_5$ and $R_7$ are each independently a $C_1$–$C_6$ alkyl or —$(CH_2)_n$—(Ar) wherein n is an integer 0, 1, 2 or 3; and Ar is phenyl or naphthyl unsubstituted or substituted with one to three substituents selected from the group consisting of hydroxy, methoxy, ethoxy, halogen, trifluoromethyl, $C_1$–$C_6$ alkyl, or —$NR_8R_9$, wherein $R_8$ and $R_9$ are each independently hydrogen or $C_1$–$C_6$ alkyl; with the proviso that when $R_2$ and at least one of $R_5$ or $R_7$ is $C_1$–$C_6$ alkyl, and Ar is not substituted with trifluoromethyl or —$NR_8R_9$, then R is —C(O)—$(CH_2)_m$—Q; or a pharmaceutically acceptable salt thereof.

2. A compound of claim 1 wherein $R_1$ is methyl or tertiarybutyl; $R_2$ and $R_3$ are each independently hydrogen, methyl or tertiarybutyl; $R_4$ is hydrogen or methyl; $R_5$ is methyl; $R_6$ is methyl or phenyl; and R is hydrogen, acetyl or succinyl.

3. A compound claim 1 wherein $R_7$ is —$(CH_2)_n$—(Ar) wherein n is an integer 0, 1, 2 or 3; and Ar is phenyl substituted with one to three —$NR_8R_9$ substituents.

4. A compound of claim 3 wherein R is hydrogen, acetyl or succinyl; $R_1$ is methyl or tertiarybutyl; $R_2$ and $R_3$ are each independently hydrogen, methyl or tertiarybutyl; $R_4$ is hydrogen or methyl; $R_5$ and $R_6$ are each methyl.

5. A compound of claim 4 wherein $R_8$ and $R_9$ are each methyl and R is hydrogen.

6. A compound of claim 1 wherein R is —C(O)—$(CH_2)_m$—Q wherein Q is hydrogen or -COOH and m is an integer 1, 2, 3 or 4.

7. A compound of claim 6 wherein $R_1$ is methyl or tertiarybutyl; $R_2$ and $R_3$ are each independently hydrogen, methyl or tertiarybutyl; $R_4$ is hydrogen or methyl; $R_5$ is methyl; $R_6$ is methyl or phenyl; and $R_8$ and $R_9$ are each methyl.

8. A method according to claim 2 wherein Z is thio.

9. A method according to claim 2 wherein Z is oxy.

10. A compound of claim 1 wherein the compound is 2,6-Di-t-butyl-4-[(diphenylmethylsilyl)methyloxy]phenol.

11. A compound of claim 1 wherein the compound is 2,6-Di-t-butyl-4-[(4-N,N-dimethylaminophenyldimethylsilyl)methyloxy]phenol.

12. A compound of claim 1 wherein the compound is 2,6-Di-t-butyl-4-[(dimethyl-4-trifluoromethylphenylsilyl)methyloxy]phenol.

13. A compound of claim 1 wherein the compound is 2,6-Di-t-butyl-4-[(dimethyl-3-trifluoromethylphenylsilyl)methyloxy]phenol.

14. A compound of claim 1 wherein the compound is 2-t-Butyl-4-[(dimethylphenylsilyl)methyloxy]phenol.

15. A compound of claim 1 wherein the compound is 2,6-Di-t-butyl-4-[(dimethylphenylsilyl)methyloxy]phenol succinic acid ester.

16. A compound of claim 1 wherein the compound is 2-t-Butyl-4-[(dimethylphenylsilyl)methyloxy]phenol succinic acid ester.

17. A compound of claim 1 wherein the compound is 2,6-Di-t-butyl-4-[(dimethylphenylsilyl)methylthio]phenol succinic acid ester.

18. A compound of claim 1 wherein the compound is 2,6-Di-t-butyl-4-[(trimethylsilyl)methylthio]phenol succinic acid ester.

19. A compound of claim 1 wherein the compound is 2-t-Butyl-4-[(dimethylphenylsilyl)methyloxy]phenol acetic acid ester.

20. A compound of claim 1 wherein the compound is 2,6-Di-t-butyl-4-[(dimethylphenylsilyl)methyloxy]phenol acetic acid ester.

21. A compound of claim 1 wherein the compound is 2,3,6-Trimethyl-4-[(dimethylphenylsilyl)methyloxy]phenol acetic acid ester.

22. A compound of claim 1 wherein the compound is 2,5-Di-t-butyl-4-[(dimethylphenylsilyl)methyloxy]phenol.

23. A compound of claim 1 wherein the compound is 2,5-Di-t-butyl-4-[(dimethylphenylsilyl)methyloxy]phenol acetic acid ester.

24. A compound of claim 1 wherein the compound is 2-t-Butyl-4-[(dimethylphenylsilyl)methylthio]phenol.

25. A compound of claim 1 wherein the compound is 2,3,6-Trimethyl-4-[(dimethylphenylsdilyl)methloxy]phenol.

26. A compound of claim 1 wherein the compound is 2,3,5-Trimethyl-4-[(dimethylphenylsilyl)methyloxy]phenol.

27. A compound of claim 1 wherein the compound is 2-t-Butyl-4-[(dimethyl-p-methoxylphenylsilyl)methyloxy]phenol.

28. A compound of claim 1 wherein the compound is 2,5-Di-t-butyl-4-[(diphenylmethylsilyl)methyloxy]phenol.

29. A compound of claim 1 wherein the compound is 2,6-Di-t-butyl-4-[(diphenylmethylsilyl)methyloxy]phenol.

30. A compound of claim 1 wherein the compound is 2,6-Di-t-butyl-4-[(methyl-di-p-methoxyphenylsilyl)methyloxy]phenol.

31. A compound of claim 1 wherein the compound is 2-t-butyl-4-[(dimethylbenzylsilyl)methyloxy]phenol.

32. A method of inhibiting the progression of atherosclerosis in a patient in need thereof comprising administering to the patient an effective antiatherosclerotic amount of a compound of claim 1.

33. A method of treating a patient for atherosclerosis comprising administering to the patient an effective antiatherosclerotic amount of a compound of claim 1.

34. A method of inhibiting peroxidation of LDL cholesterol in a patient in need thereof comprising administering to the patient an effective antioxidant amount of a compound of claim 1.

35. A method of lowering plasma cholesterol level in a patient in need thereof comprising administering to the patient a plasma cholesterol lowering amount of a compound of claim 1.

36. A method of inhibiting cytokine-induced expression of vascular cell adhesion molecule-1 and/or intercellular adhesion molecule-1 in a patient in need thereof comprising administering to the patient an effective vascular cell adhesion molecule-1 and/or intercellular adhesion molecule-1 inhibiting amount of a compound of claim 1.

37. A method of treating a patient afflicted with a chronic inflammatory disease comprising administering to the patient a therapeutically effective amount of a compound of claim 1.

38. A method according to claim 37 wherein the inflammatory disease is asthma.

39. A method according to claim 37 wherein the inflammatory disease is chronic inflammation.

40. A method according to claim 37 wherein the inflammatory disease is rheumatoid arthritis.

41. A method according to claim 37 wherein the inflammatory disease is autoimmune diabetes.

42. A method according to claim 37 wherein the inflammatory disease is transplant rejection.

43. A method according to claim 37 wherein the inflammatory disease is tumor angiogenesis.

* * * * *

UNITED STATES PATENT AND TRADEMARK OFFICE
CERTIFICATE OF CORRECTION

PATENT NO. : 5,608,095

DATED : March 4, 1997

INVENTOR(S) : Roger A. Parker, et al.

It is certified that error appears in the above-identified patent and that said Letters Patent is hereby corrected as shown below:

At column 8, line 47, the patent reads "MDL104,5599" and should read --MDL 104,599--.
At column 9, line 12, the patent reads "dimethylaminophenyylsilane" and should read --dimethylaminophenylsilane--.
At column 9, line 19 and at column 11, line 19, the patent reads "arate" and should read --a rate--.
At column 9, line 51, the patent reads "methoxy" and should read --methyloxy--.
At column 9, line 65, the patent reads "(~10," and should read --(~1:10,--.
At column 11, line 12, the patent reads "trifluoromethhylphenylsilane" and should read --trifluoromethylphenylsilane--.
At column 16, line 61, the patent reads "wads" and should read --was--.
At column 17, line 26, at column 30, line 24 and at column 46, line 44, the patent reads "dimethylphenylsdilyl" and should read --dimethylphenylsilyl--.

At column 20, line 10, in the structure, the patent reads 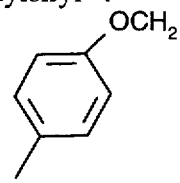 and should read 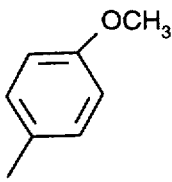.

UNITED STATES PATENT AND TRADEMARK OFFICE
CERTIFICATE OF CORRECTION

PATENT NO. : 5,608,095

DATED : March 4, 1997

INVENTOR(S) : Roger A. Parker, et al.

It is certified that error appears in the above-identified patent and that said Letters Patent is hereby corrected as shown below:

At column 27, line 15, the patent reads "an suitable" and should read --a suitable--.
At column 35, line 66, the patent reads "Anglogenesis" and should read --Angiogenesis--.
At column 36, line 26, the patent reads "from marginal" and should read --from a marginal--.
At column 37, line 49, the patent reads "Absrobances" and should read --Absorbances--.
At column 41, line 30, the patent reads "Control" and should read --% control--.

Signed and Sealed this

Fifteenth Day of September, 1998

Attest:

BRUCE LEHMAN

Attesting Officer

Commissioner of Patents and Trademarks